(12) United States Patent
Lee et al.

(10) Patent No.: US 10,683,512 B2
(45) Date of Patent: Jun. 16, 2020

(54) METHOD FOR PREPARING VARIOUS LACTAM

(71) Applicant: KOREA ADVANCED INSTITUTE OF SCIENCE AND TECHNOLOGY, Daejeon (KR)

(72) Inventors: Sang Yup Lee, Daejeon (KR); Tong Un Chae, Daejeon (KR); Chan Woo Song, Daejeon (KR)

(73) Assignee: KOREA ADVANCED INSTITUTE OF SCIENCE AND TECHNOLOGY, Daejeon (KR)

( * ) Notice: Subject to any disclaimer, the term of this patent is extended or adjusted under 35 U.S.C. 154(b) by 307 days.

(21) Appl. No.: 15/545,311

(22) PCT Filed: Apr. 11, 2016

(86) PCT No.: PCT/KR2016/003758
§ 371 (c)(1),
(2) Date: Jul. 20, 2017

(87) PCT Pub. No.: WO2016/167519
PCT Pub. Date: Oct. 20, 2016

(65) Prior Publication Data
US 2018/0037896 A1 Feb. 8, 2018

(30) Foreign Application Priority Data

Apr. 13, 2015 (KR) .......................... 10-2015-0051994
Apr. 8, 2016 (KR) .......................... 10-2016-0043539

(51) Int. Cl.
| | |
|---|---|
| C12N 15/52 | (2006.01) |
| C12N 15/79 | (2006.01) |
| C12P 17/10 | (2006.01) |
| C12N 9/10 | (2006.01) |
| A61K 35/742 | (2015.01) |
| C08G 69/14 | (2006.01) |

(52) U.S. Cl.
CPC ............ *C12N 15/79* (2013.01); *A61K 35/742* (2013.01); *C08G 69/14* (2013.01); *C12N 9/13* (2013.01); *C12N 15/52* (2013.01); *C12P 17/10* (2013.01)

(58) Field of Classification Search
CPC ..................................................... C12N 15/52
See application file for complete search history.

(56) References Cited

U.S. PATENT DOCUMENTS

| | | | |
|---|---|---|---|
| 8,592,189 B2 | 11/2013 | Burgard et al. | |
| 2010/0324257 A1 | 12/2010 | Karau et al. | |
| 2012/0028320 A1 | 2/2012 | Raemakers-Franken et al. | |
| 2012/0149077 A1 | 6/2012 | Shaw et al. | |
| 2013/0095540 A1 | 4/2013 | Burgard et al. | |
| 2013/0303723 A1 | 11/2013 | Burk et al. | |
| 2014/0134681 A1 | 5/2014 | Raemakers-Franken et al. | |

FOREIGN PATENT DOCUMENTS

| | | |
|---|---|---|
| CN | 1714146 A | 12/2005 |
| EP | 0307247 A2 | 3/1989 |
| JP | 2005-525100 A | 8/2005 |
| JP | 2012-525856 A | 10/2012 |
| JP | 2014-521365 A | 8/2014 |
| KR | 10-2012-0034640 A | 4/2012 |
| WO | 9108291 A2 | 6/1991 |
| WO | 2008095927 A1 | 8/2008 |

OTHER PUBLICATIONS

Horitsu, H., et al., "Studies on L-Glutamate Decarboxylase Activity in *E. coli* Part III. Physiological Role of L-Glutamate Decarboxylase", "Gifu University, Gifu", 1972, pp. 191-195, vol. 46, No. 4, Publisher: Chukyo Women's University, Ohbu, Aichi.

Adkins, J., et al., "Engineering *Escherichia coli* for Renewable Production of the 5-Carbon Polyamide Building-Blocks 5-Aminovalerate and Glutarate", "Biotechnology and Bioengineering", Jun. 2013, pp. 1726-1734, vol. 110, No. 6.

Eikmanns, B. J., et al., "A family of Corynebacterium glutamicum/ *Escherichia coli* shuttle vectors for cloning, controlled gene expression, and promoter probing", "Gene", 1991, pp. 93-98, vol. 102.

Herrmann, G., et al., "Two beta-alanyl-CoA:ammonia lyases in Clostridium propionicum", "The FEBS Journal", 2005, pp. 813-821, vol. 272.

Koetsier, M. J., et al., "Aminoacyl-coenzyme A synthesis catalyzed by a CoA ligase from Penicillium chrysogenum", "FEBS Letters", 2011, pp. 893-898, vol. 585.

(Continued)

*Primary Examiner* — Tekchand Saidha

(74) *Attorney, Agent, or Firm* — Hultquist, PLLC; Steven J. Hultquist

(57) ABSTRACT

The present disclosure relates to a recombinant microorganism having a lactam production capacity from an omega-amino acid, into which a gene encoding a beta-alanine coenzyme A transferase on a microorganism which has an omega-amino acid biosynthetic metabolic pathway inherently or an omega-amino acid biosynthetic metabolic pathway is introduced, and a method for producing a variety of lactams and omega-amino acyl-CoAs using the same.

The recombinant microorganism and the method for producing the lactam according to the present disclosure are useful in producing a variety of lactams such as propiolactam, 2-pyrrolidone, valerolactam, caprolactam, and heptanolactam from a variety of omega-amino acids.

19 Claims, 15 Drawing Sheets
(13 of 15 Drawing Sheet(s) Filed in Color)
Specification includes a Sequence Listing.

(56) References Cited

OTHER PUBLICATIONS

Lee, K. H., et al., "Systems metabolic engineering of *Escherichia coli* for L-threonine production", "Molecular Systems Biology", 2007, pp. 1-8, vol. 3, No. 149.

Lee, P. C., et al., "Batch and continuous cultivation of Anaerobiospirillum succiniciproducens for the production of succinic acid from whey", "Applied Microbiology and Biotechnology", 2000, pp. 23-27, vol. 54.

Lee, P. C., et al., "Succinic Acid Production with Reduced By-Product Formation in the Fermentation of Anaerobiospirillum succiniciproducens Using Glycerol as a Carbon Source", "Biotechnology and Bioengineering", Jan. 5, 2001, pp. 41-48, vol. 72, No. 1.

Lee, P. C., et al., "Isolation and characterization of a new succinic acid-producing bacterium, Mannheimia succiniciproducens MBEL55E, from bovine rumen", "Applied Microbiology and Biotechnology", Feb. 8, 2002, pp. 663-668, vol. 58.

Lee, P. C., et al., "Batch and continuous cultures of Mannheimia succiniciproducens MBEL55E for the production of succinic acid from whey and corn steep liquor", "Bioprocess and Biosystems Engineering", Oct. 6, 2003, pp. 63-67, vol. 26.

Lee, P. C., et al., "Biological conversion of wood hydrolysate to succinic acid by Anaerobiospirillum succiniciproducens", "Biotechnology Letters", 2003, pp. 111-114, vol. 25.

Li, H., et al., "Production of gamma-aminobutyric acid by Lactobacillus brevis NCL912 using fed-batch fermentation", "Microbial Cell Factories", 2010, pp. 1-7, vol. 9, No. 85.

Park, S. J., et al., "Metabolic engineering of *Escherichia coli* for the production of 5-aminovalerate and glutarate as C5 platform chemicals", "Metabolic Engineering", Dec. 14, 2012, pp. 42-47, vol. 16.

Shi, F., et al., "Synthesis of c-aminobutyric acid by expressing Lactobacillus brevis-derived glutamate decarboxylase in the Corynebacterium glutamicum strain ATCC 13032", "Biotechnology Letters", Aug. 9, 2011, pp. 2469-2474, vol. 33.

Shi, F., et al., "Enhancement of c-aminobutyric acid production in recombinant Corynebacterium glutamicum by co-expressing two glutamate decarboxylase genes from Lactobacillus brevis", "Journal of Industrial Microbiology & Biotechnology", Aug. 9, 2013, pp. 1285-1296, vol. 40.

Takahashi, C., et al., "Robust production of gamma-amino butyric acid using recombinant Corynebacterium glutamicum expressing glutamate decarboxylase from *Escherichia coli*", "Enzyme and Microbial Technology", 2012, pp. 171-176, vol. 51.

Note: For the non-patent literature citations that no month of publication is indicated, the year of publication is more than 1 year prior to the effective filing date of the present application.

Zaboura, M., et al, "Regulation of y-Aminobutyric Acid Degradation in *Escherichia coli* by Nitrogen Metabolism Enzymes", "Journal of Bacteriology", Feb. 1978, p. 447-451, vol. 133, No. 2.

METHOD FOR PREPARING VARIOUS LACTAM

CROSS-REFERENCE TO RELATED APPLICATIONS

This application is a U.S. national phase under the provisions of 35 U.S.C. § 371 of International Patent Application No. PCT/KR2016/003758 filed Apr. 11, 2016, which in turn claims priority of Korean Patent Application No. 10-2015-0051994 filed Apr. 13, 2015 and Korean Patent Application No. 10-2016-0043539 filed Apr. 8, 2016. The disclosures of such international patent application and Korean priority patent applications are hereby incorporated herein by reference in their respective entireties, for all purposes.

BACKGROUND

Field

The present disclosure relates to a method for preparing a lactam using an enzyme, and more particularly, to a method for preparing a lactam using an enzyme, which converts an omega-amino acid into an omega-amino acyl-CoA, or a recombinant microorganism into which a gene encoding the enzyme is introduced.

Description of the Related Art

Recently, due to the problem of oil depletion and environmental problems, a lot of attention has been focused on the production of various sustainable value-added chemical products using microorganisms. Many studies have been conducted to produce various lactams, which are precursors of nylon, among the various value-added compounds. However, until the present, there have not been successful examples of production of various lactams using recombinant microorganisms.

However, there are many reports of recombinant microorganisms that produce omega-amino acids, which are precursors of lactams using conventional metabolic engineering methods. Known examples were the production of omega-amino acids such as gamma-aminobutyric acid (GABA), 5-aminovaleric acid (5AVA), and 6-aminocaproic acid (6ACA), which are precursors of 2-pyrrolidone, valerolactam, and caprolactam as typical examples regarding a lactam.

First, production studies of GABA are being conducted using recombinant microorganisms based on *Corynebacterium* (Shi et al., Biotechol. Lett. 33:2469-2474 2011; Shi et al., J. Ind. Microbiol. Biotechnol. 40:1285-1296, 2013; Takahashi et al., Enzyme Microb. Tech. 51:171-176, 2012) and Lactic acid bacteria (Li et al., Microb. Cell. Fact. 9:85, 2010). 5AVA was produced using *Escherichia coli* (Park et al., Metab. Eng. 16:42-47, 2013; Adkins et al., Biotechnol. Bioeng. 110:1726-1734, 2013). Finally, 6ACA was successfully patented for 6ACA production (US 2014/0134681) through 5-formylvaleric acid (US 2012/0028320 A1) based on methanogens metabolic pathway.

Direct lactam production using recombinant microorganisms has not been reported, but there is a patent designing a metabolic circuit capable of producing caprolactam in microorganisms, which is one of the most demanding lactams (US 2013/0303723 A1). However, in this patent, there are no actual data about caprolactam production and enzyme that could actually cause such metabolic pathway to occur.

Accordingly, the present inventors have made efforts to develop a method for efficiently producing various lactams using microorganisms. As a result, they have found that an enzyme that takes an omega-amino acid as a substrate and converts it into omega-aminoacyl-CoA. It has been confirmed that a lactam can be prepared using the enzyme itself or a recombinant microorganism into which the gene is introduced, thereby completing the present disclosure.

SUMMARY

An object of the present disclosure is to provide a recombinant microorganism into which a gene encoding an enzyme is introduced, in which the enzyme converts an omega-amino acid into an omega-amino acyl-CoA.

Another object of the present disclosure is to provide a method for preparing various lactams from omega-amino acids using the recombinant microorganism.

Still another object of the present disclosure is to provide a method for preparing various lactams from omega-amino acids using an enzyme that converts omega-amino acids into omega-amino acyl-CoAs.

Yet another object of the present disclosure is to provide a method for preparing various omega-amino acyl-CoAs from omega-amino acids using a recombinant microorganism into which a gene encoding an enzyme is introduced, in which the enzyme converts omega-amino acids to omega-amino acyl-CoAs.

Yet another object of the present disclosure is to provide a method for preparing various omega-amino acyl-CoAs from omega-amino acids using an enzyme that converts omega-amino acids into omega-amino acyl-CoAs.

In order to achieve the above object, the present disclosure provides a recombinant microorganism having an ability to produce lactam from an omega-amino acid, wherein a gene encoding a beta-alanine coenzyme A transferase is introduced into a microorganism which has an omega-amino acid biosynthetic metabolic pathway inherently or an omega-amino acid biosynthetic metabolic pathway is introduced.

The present disclosure also provides a method for preparing a lactam from an omega-amino acid using a recombinant microorganism into which a beta-alanine coenzyme A transferase gene is introduced, in which the method includes the steps of: (a) culturing the recombinant microorganism to produce the lactam; and (b) recovering the produced lactam.

The present disclosure also provides a method for preparing a lactam from an omega-amino acid using beta-alanine coenzyme A transferase, in which the method includes the steps of: (a) mixing the beta-alanine coenzyme A transferase with a reaction solution containing the omega-amino acid and then reacting to prepare an omega-amino acyl-CoA; and (b) preparing a lactam by forming a ring structure of the produced omega-amino acyl-CoA.

The present disclosure also provides a method for preparing an omega-amino acyl-CoA from an omega-amino acid using a recombinant microorganism into which a beta-alanine coenzyme A transferase gene is introduced, in which the method includes the steps of: (a) culturing the recombinant microorganism to produce the omega-amino acyl-CoA; and (b) recovering the produced omega-amino acyl-CoA.

The present disclosure also relates to a method for preparing an omega-amino acyl-CoA from an omega-amino acid using a beta-alanine coenzyme A transferase, in which the method includes a step of mixing a beta-alanine coenzyme A transferase in a reaction solution containing the omega-amino acid and then reacting to prepare the omega-amino acyl-CoA.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION OF THE PREFERRED EMBODIMENT

Unless otherwise defined, all technical and scientific terms used herein have the same meaning as commonly understood by one of ordinary skill in the art to which the present disclosure belongs. In general, the nomenclature used herein is well known and commonly used in the art.

Figure 1:
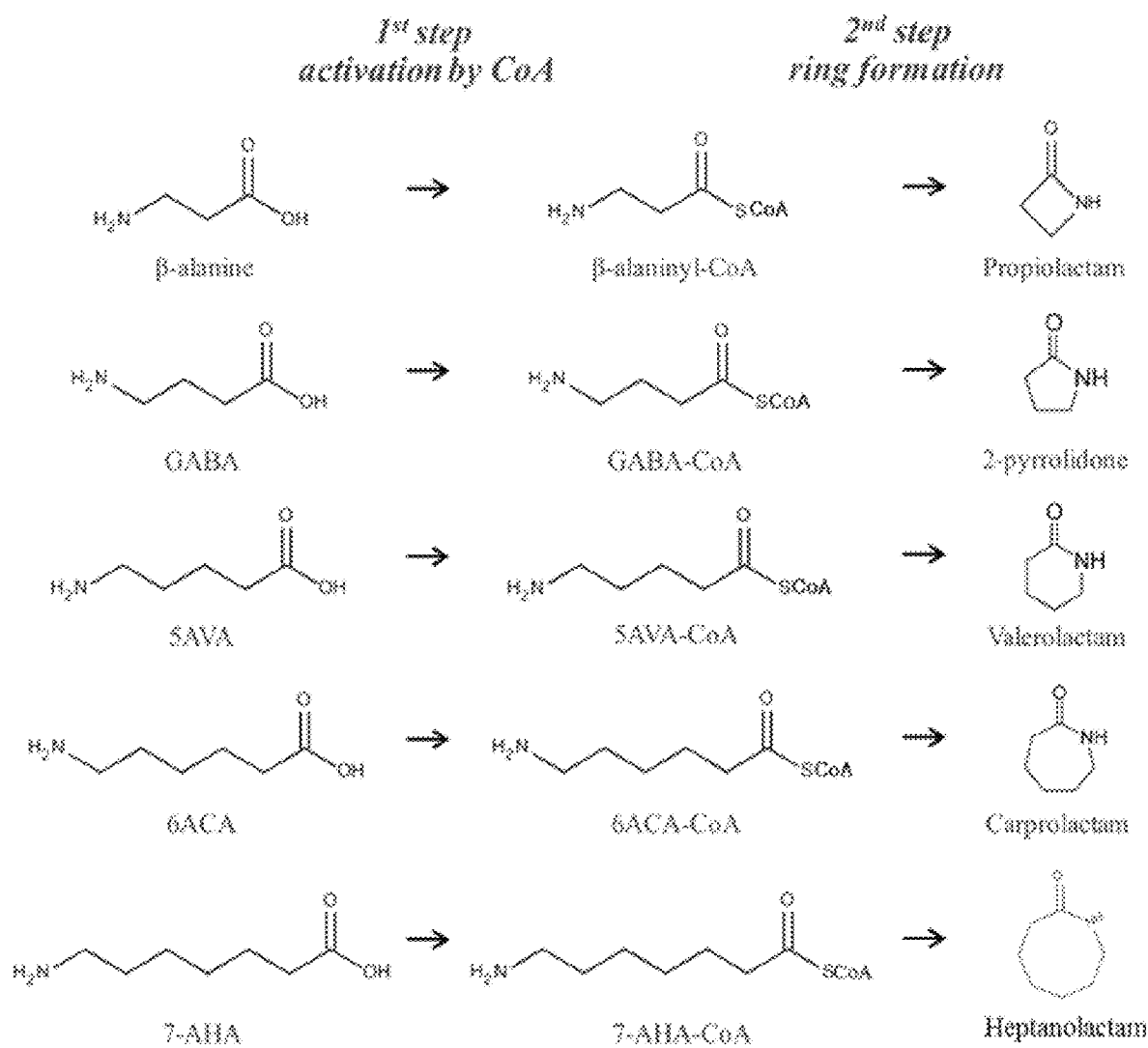
FIG. 1 shows pathways for preparing various lactams through omega-amino acyl coenzyme A transferases from omega-amino acids.

In the present disclosure, it is confirmed that an enzyme, beta-alanine coenzyme A transferase, takes various omega-amino acids other than beta-alanine, which is a natural omega-amino acid substrate, as a substrate to form a corresponding omega-amino acyl coenzyme A, such omega-amino acyl coenzyme A is converted into a corresponding lactam without the help of enzymes, and thus it is possible to establish a system capable of preparing various lactams from omega-amino acids using enzymes (FIG. 1).

In the present disclosure, an experiment was conducted to investigate the possibility of production of a lactam using a microorganism into which a gene encoding a beta-alanine coenzyme A transferase, which is one of the enzymes that convert an omega-amino acid into an omega-amino acyl-CoA, was introduced. As a result, it was confirmed that a lactam was produced when a microorganism, into which the gene encoding the enzyme was introduced, was used.

That is, in one embodiment of the present disclosure, in order to confirm whether 2-pyrrolidone is produced through GABA coenzyme A by GABA which is a representative omega-amino acid in microorganisms, a pTac15k_act vector, in which act, a gene encoding a beta-alanine coenzyme A transferase, was cloned, was prepared (See FIG. 8), and then was introduced into wild Escherichia coli. Further, a glutamic acid, a precursor of GABA, was supplied as a carbon source with glucose to provide GABA in microorganisms. As a result of culturing the recombinant microorganism under the above culture conditions, it was able to be confirmed that 2-pyrrolidone, a kind of lactam, was produced in the microorganism culture solution (See FIG. 9).

Therefore, in an aspect of the present disclosure, it relates to a recombinant microorganism having an ability to produce lactam from an omega-amino acid, wherein a gene encoding a beta-alanine coenzyme A transferase is introduced into a microorganism which has an omega-amino acid biosynthetic metabolic pathway inherently or an omega-amino acid biosynthetic metabolic pathway is introduced.

The term "inhere" in the present disclosure means a metabolic pathway in which a microorganism has its own, without adding it to a microorganism by genetic recombination. For example, the metabolic pathway of Escherichia coli producing GABA from glutamic acid, which is performed in one embodiment of the present disclosure, is a pathway of biosynthesizing glutamic acid from glucose through glycolysis, and then by producing GABA through intrinsic glutamic acid decarboxylase (GadA or GadB).

In the present disclosure, the omega-amino acid biosynthetic pathway may be introduced by introducing a corresponding gene. For example, it can be characterized by introducing a metabolic pathway for biosynthesis of 5-aminovaleric acid (5AVA) from lysine in Escherichia coli.

In the present disclosure, the 5-aminovaleric acid biosynthetic pathway from the lysine may be, but not limited to, characterized by introducing a gene encoding delta-aminovaleramidase and a gene encoding lysine 2-monooxygenase, and the gene encoding delta-aminovaleramidase is a davA gene derived from Pseudomonas putida and the gene encoding lysine 2-monooxygenase is a davB gene derived from Pseudomonas putida.

In the present disclosure, the gene encoding the beta-alanine coenzyme A transferase may be, but not limited to, characterized to be an act derived from Clostridium propionicum.

In the present disclosure, the act gene derived from Clostridium propionicum may be, but not limited to, characterized by being described by SEQ ID NO: 1.

In the present disclosure, the beta-alanine coenzyme A transferase may be, but not limited to, characterized by being described by SEQ ID NO: 2.

In the present disclosure, the enzyme may be characterized in that the homology, that is, the sequence similarity is 50% or more, preferably 60% or more, and more preferably, 70% or more.

In the present disclosure, the lactam may be any chemical substance characterized in that it has a heterocyclic ring structure and has an amide bond in the ring, but may be preferably characterized to be one selected from the group consisting of propiolactam, 2-pyrrolidone, valerolactam, caprolactam, heptanolactam, octanolactam, nonanolactam, decanolactam, undecanolactam, and dodecanolactam.

In the present disclosure, the omega-amino acid may be any chemical substance characterized in that it has an amine and a carboxylic acid functional group at the same time, but may be preferably characterized to be one selected from the group consisting of beta-alanine, gamma-aminobutyric acid (GABA), 5-aminovaleric acid (5AVA), 6-aminocaproic acid (6ACA), 7-aminoheptanoic acid (7AHA), 8-aminooctanoic acid, 9-aminononanoic acid, 10-aminodecanoic acid, 11-aminoundecanoic acid, and 12-aminododecanoic acid.

In the present disclosure, the beta alanine may be, but not limited to, characterized by having a pathway of biosynthesizing by L-aspartate-α-decarboxylase from aspartic acid, the GABA may be, but not limited to, characterized by having a pathway of biosynthesizing by glutamic acid carboxylase (GadA or GadB) from glutamic acid, the 5AVA may be characterized by having a pathway of biosynthesizing by delta-aminovaleramidase (DavA) and lysine 2-monooxygenase (DavB) from lysine, 6ACA and 7AHA may be characterized by having a pathway of biosynthesizing by homocitrate synthase, 3-isopropylmalate dehydratase, isopropylmalate/isohomocitrate dehydrogenase, branched-chain α-ketoacid decarboxylase, and pyruvate transaminase from alpha-keto glutamic acid.

In the present disclosure, the omega-amino acids may be, but not limited to, characterized by being biosynthesized from a carbon source selected from the group consisting of monosaccharides, disaccharides, and polysaccharides including glucose, sucrose, galactose, maltose, xylose, glycerol, fructose and sugar cane.

In the present disclosure, the recombinant microorganism may be any microorganism capable of producing omega-amino acid, which is a precursor thereof, or using as a carbon source and may be preferably characterized to be one selected from the group consisting of bacteria, yeast, and fungi.

In the present disclosure, the bacteria may be, but not limited to, characterized to be one selected from the group consisting of *Corynebacterium* genus and *Escherichia coli*.

In another aspect of the present disclosure, it relates to a method for preparing a lactam from an omega-amino acid, in which the method includes the steps of: (a) culturing the recombinant microorganism according to above specification to produce a lactam; (b) recovering the produced lactam.

In the present disclosure, the culturing process of the recombinant microorganism can be carried out using a conventionally known culturing method. Medium other than a sweeten liquid such as whey and a corn steep liquor (CSL) can be used and various methods such as a fed-batch culture and a continuous culture can be used in addition to the specific culture medium and the specific culture method used in the examples of the present disclosure (Lee et al., *Bioprocess Biosyst. Eng.*, 26: 63, 2003; Lee et al., *Appl. Microbiol. Biotechnol.*, 58: 663, 2002; Lee et al., *Biotechnol. Lett.*, 25: 111, 2003; Lee et al., *Appl. Microbiol. Biotechnol.*, 54: 23, 2000; Lee et al., *Biotechnol. Bioeng.*, 72: 41, 2001).

Meanwhile, it was predicted that when the enzyme was used under in vitro condition, various lactams could be prepared from omega-amino acids.

Figure 3:
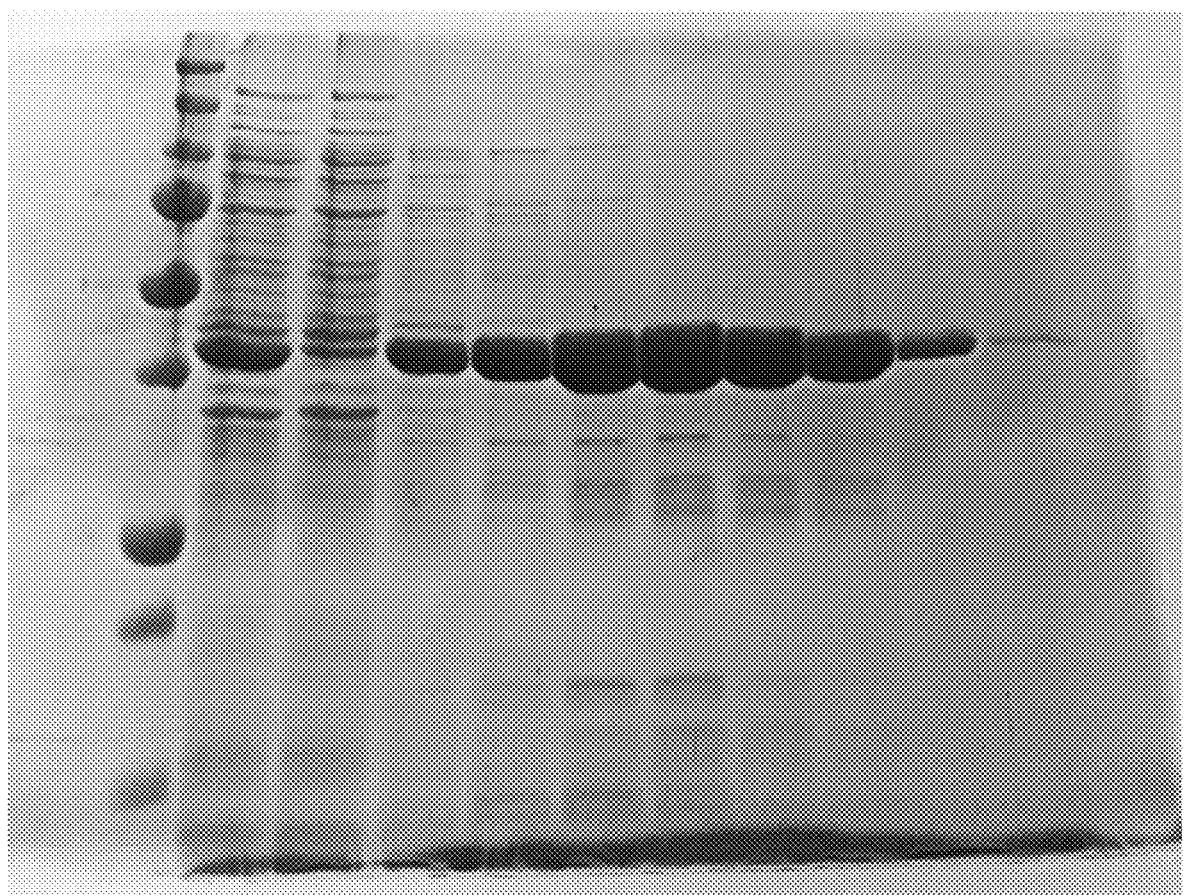
FIG. 3 is an SDS-PAGE photograph of a purified beta-alanine coenzyme A transferase.
Figure 4:
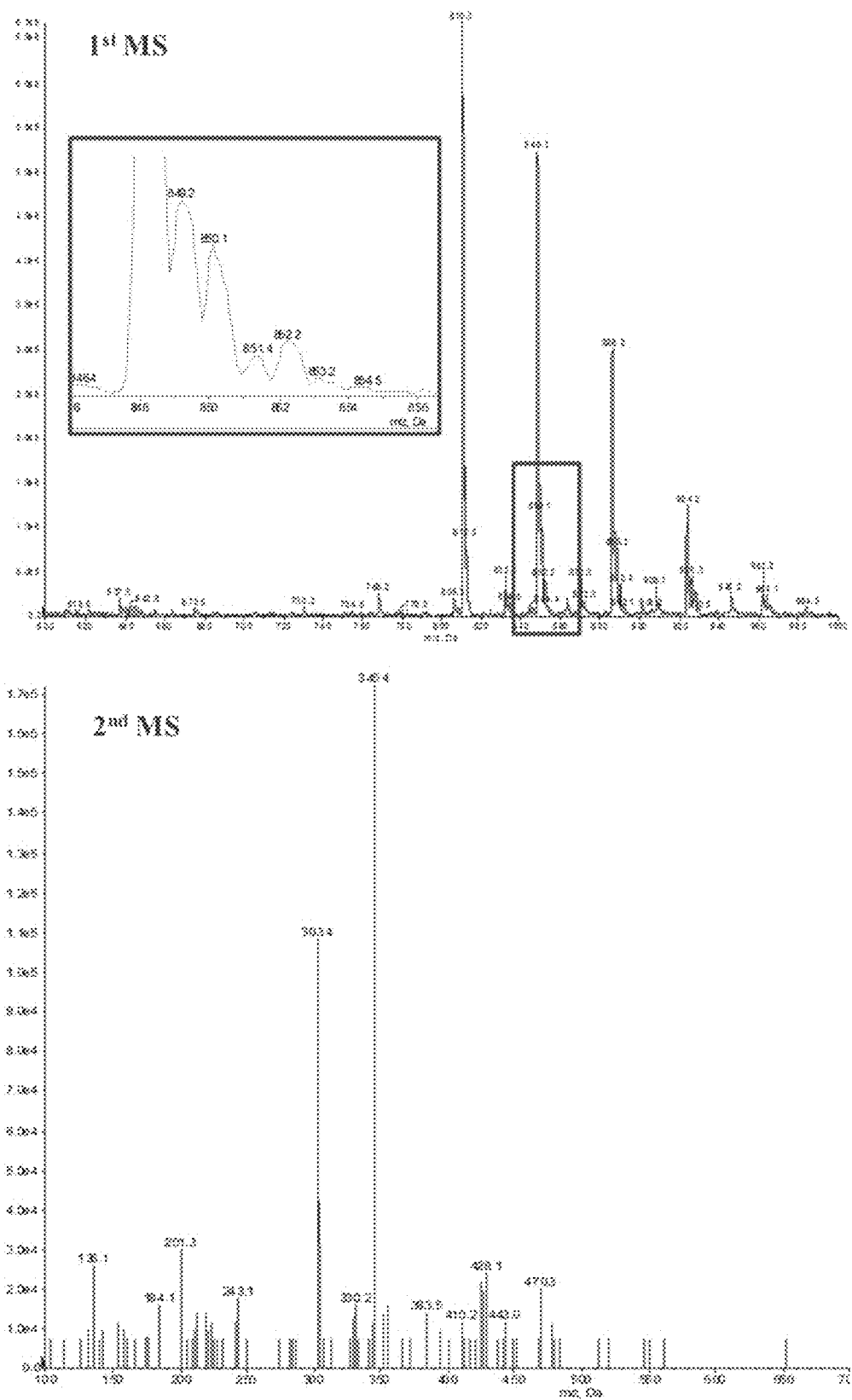
FIG. 4 shows the results of analysis of GABA-CoA prepared under in vitro condition using an enzyme, that is, a beta-alanine coenzyme A transferase.
Figure 5:
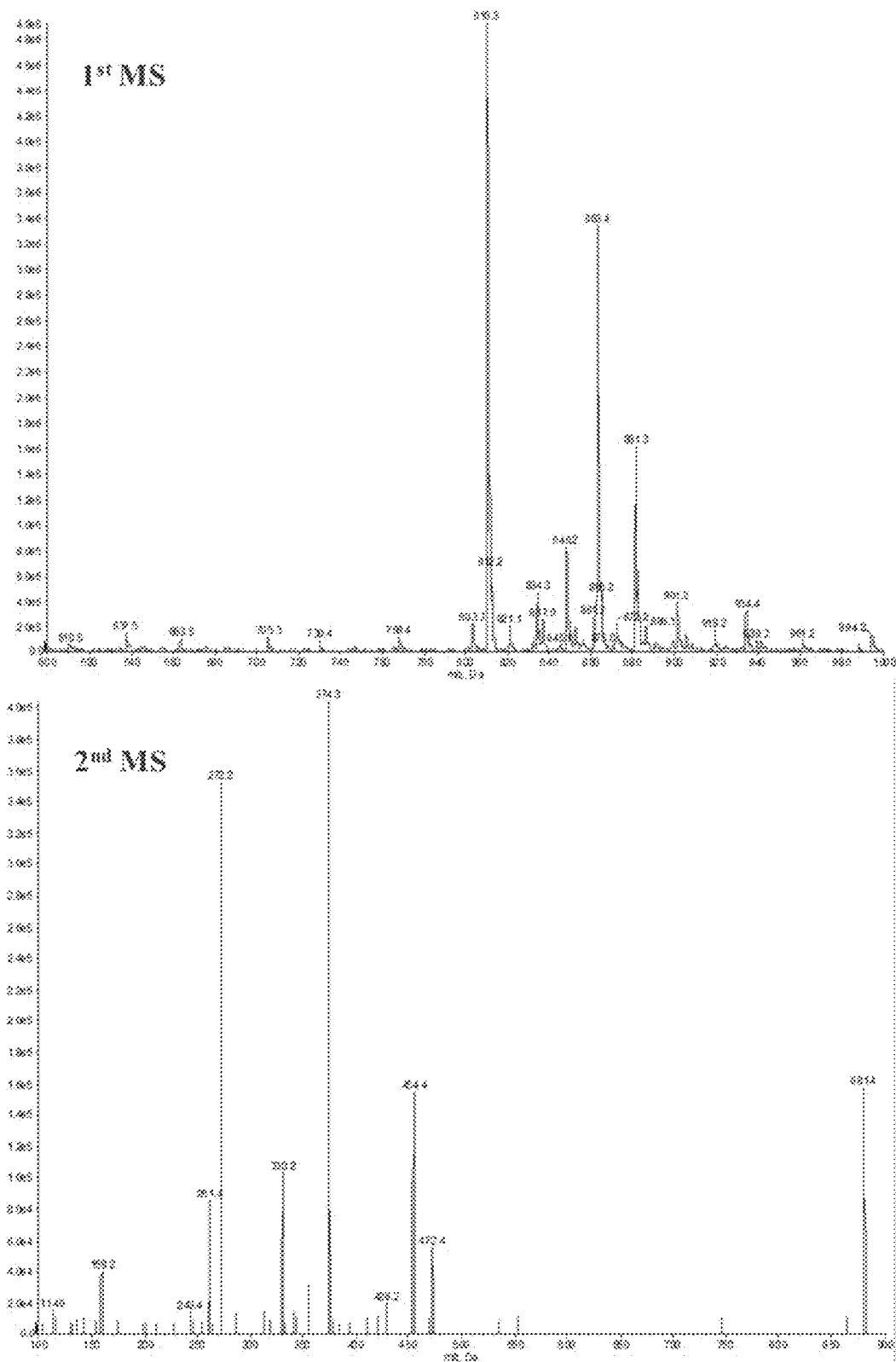
FIG. 5 shows the results of analysis of 6ACA-CoA prepared under in vitro condition using an enzyme, that is, a beta-alanine coenzyme A transferase.
Figure 10:
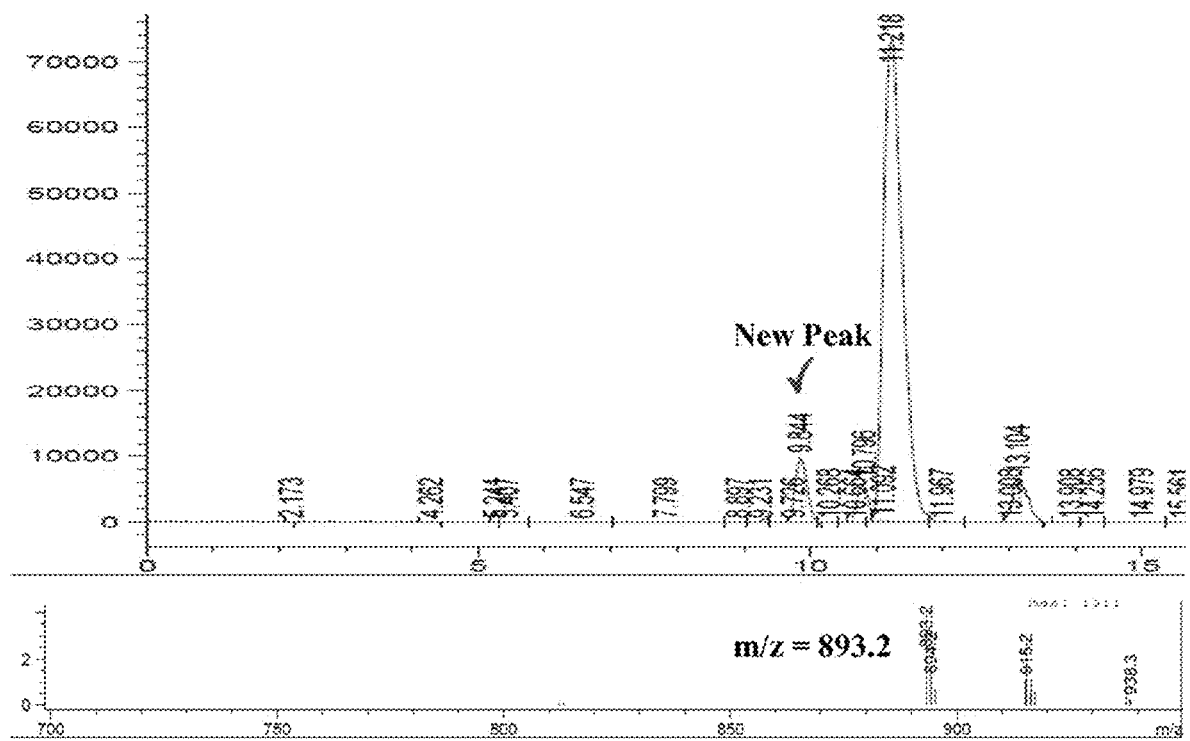
FIG. 10 shows the results of analysis of 7AHA-CoA prepared under in vitro condition using an enzyme, that is, a beta-alanine coenzyme A transferase.

In another exemplary embodiment of the present disclosure, an enzyme assay was performed to confirm that the beta-alanine coenzyme A transferase acts on the omega-amino acids such as GABA, 6ACA, and 7AHA as well as beta-alanine, a natural substrate. First, to obtain a purified enzyme, a pET30α_his_act vector was prepared by cloning a his-act gene encoding a beta-alanine coenzyme A transferase to which his tag was attached (FIG. 2), and the beta-alanine coenzyme A transferase with the his tag was purified (FIG. 3). The purified protein, acetyl coenzyme A, and GABA, 6ACA or 7AHA were added to perform the enzyme assay. Thereafter, the production of GABA coenzyme A, 6ACA coenzyme A, and 7AHA coenzyme A, omega-amino acyl coenzyme A forms, in the respective omega-amino acids was confirmed using HPLC-MS/MS or HPLC-MS (FIGS. 4, 5, and 10).

Figure 6:
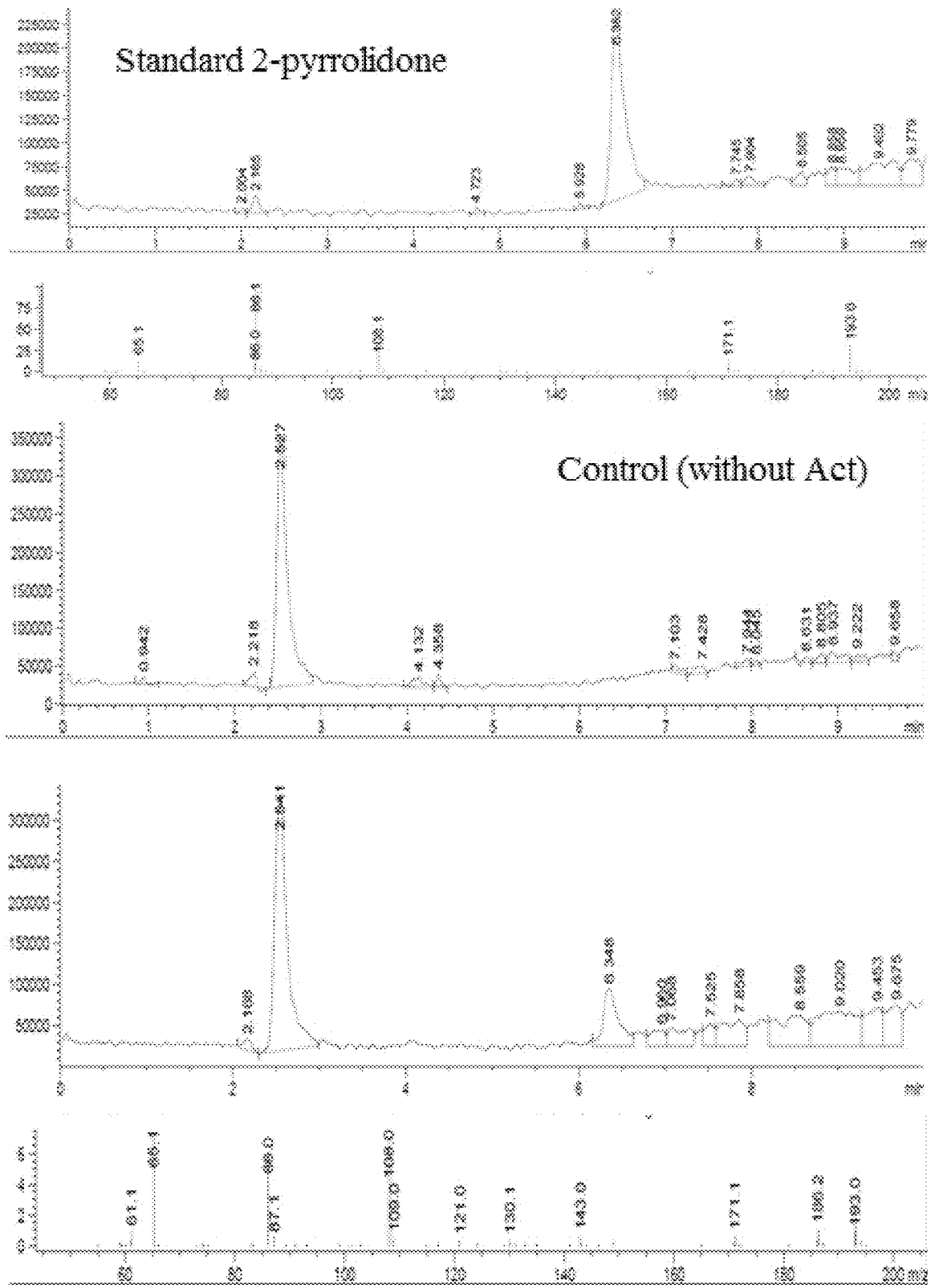
FIG. 6 shows the results of analysis of 2-pyrrolidone prepared under in vitro condition using an enzyme, that is, a beta-alanine coenzyme A transferase.
Figure 7:
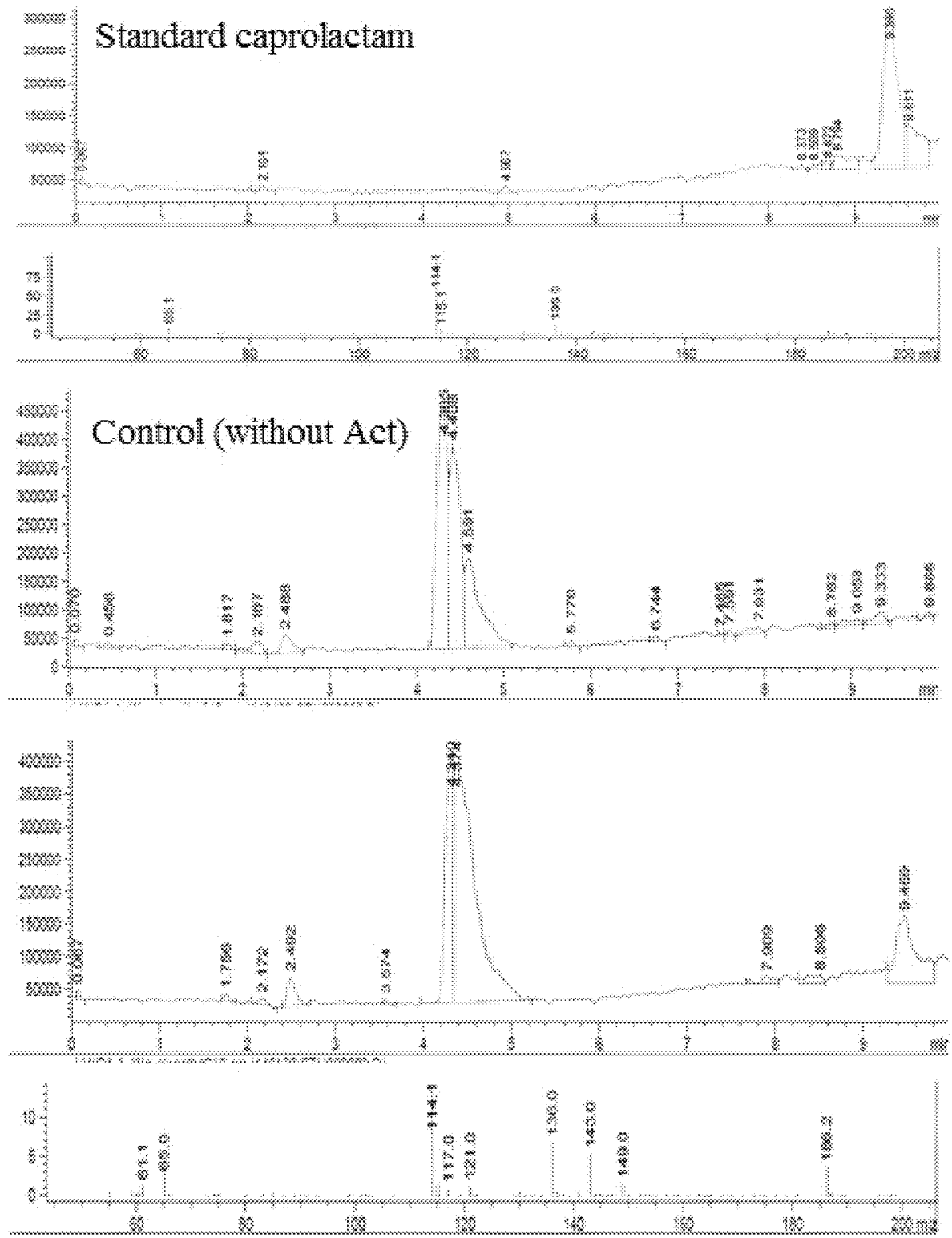
FIG. 7 shows the results of analysis of caprolactam prepared under in vitro condition using an enzyme, that is, a beta-alanine coenzyme A transferase.
Figure 11:
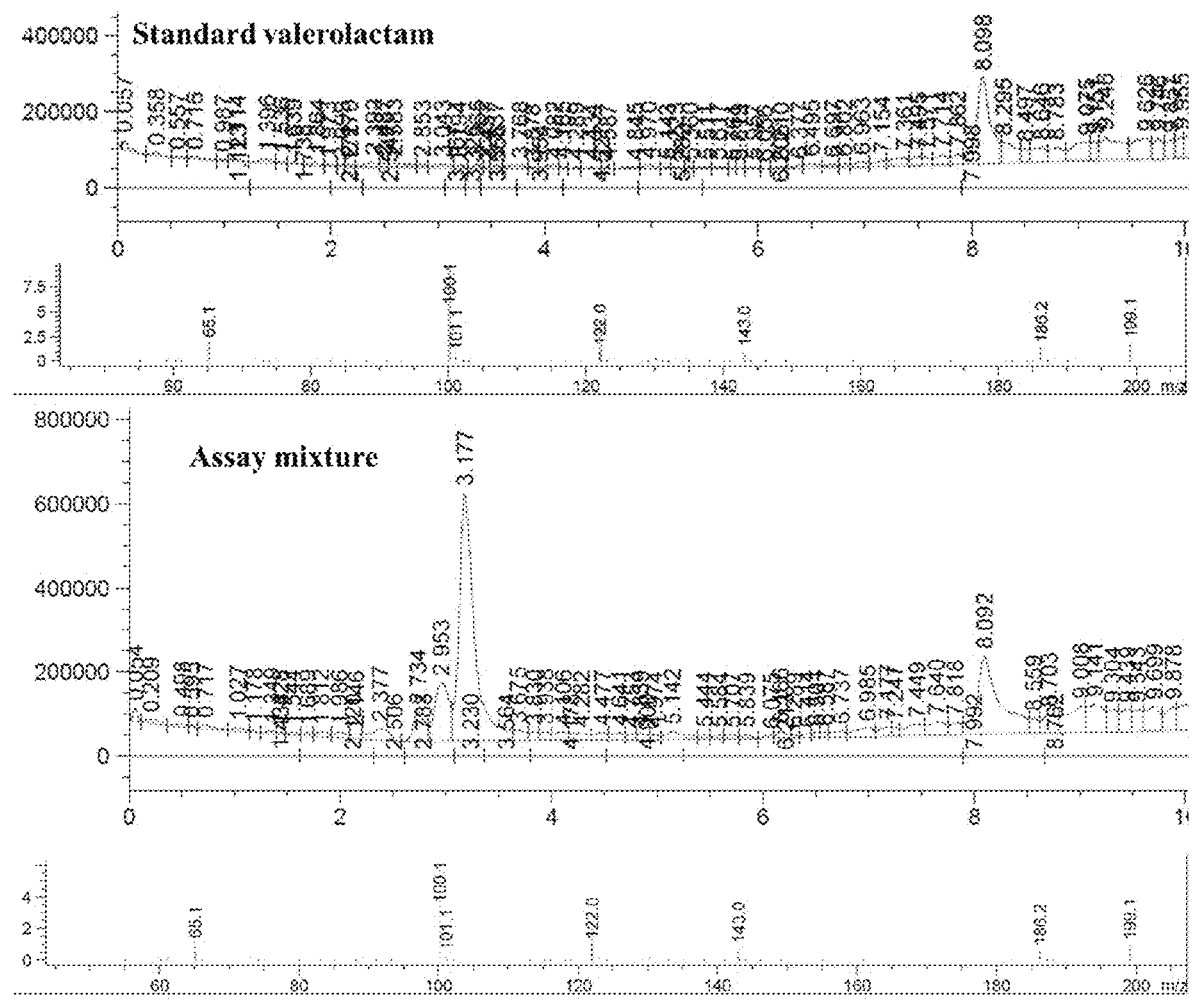
FIG. 11 shows the results of analysis of valerolactam prepared under in vitro condition using an enzyme, that is, a beta-alanine coenzyme A transferase.
Figure 12:
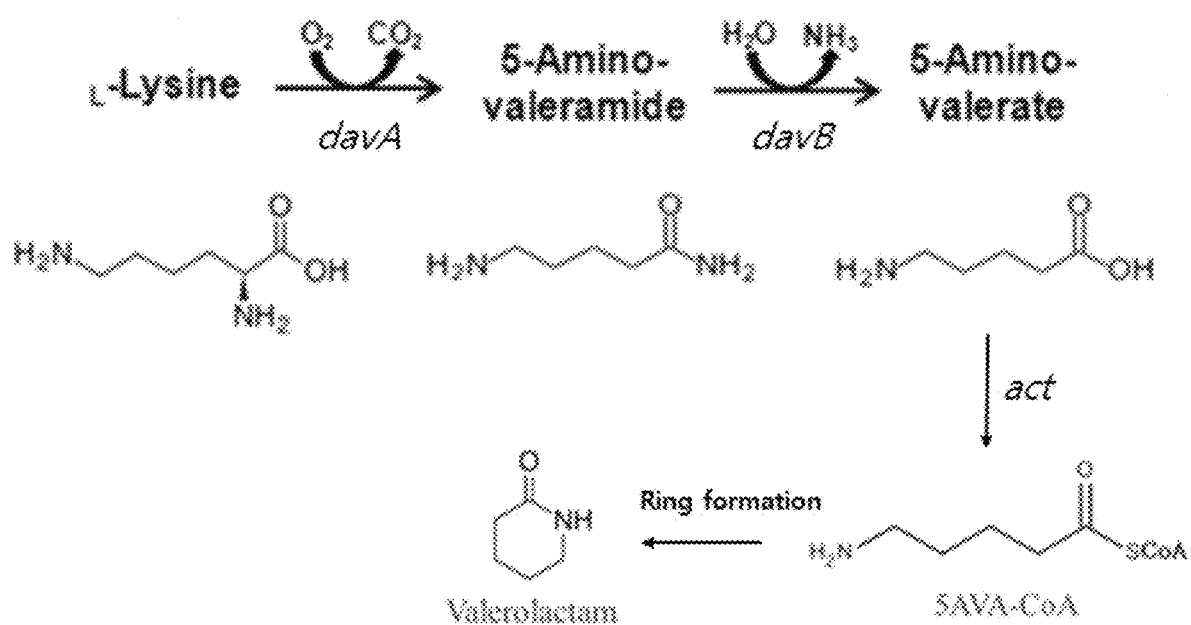
FIG. 12 shows a metabolic pathway to prepare valerolactam from lysine performed in one exemplary embodiment of the present disclosure.

In still another exemplary embodiment of the present disclosure, experiments were conducted to confirm that GABA coenzyme A, 5AVA coenzyme A, and 6ACA coenzyme A, which are one of the representative omega-amino acyl-CoA, are converted to the corresponding lactam without the help of enzymes. Enzyme assay showed that GABA coenzyme A, 5AVA coenzyme A, and 6ACA coenzyme A were produced without adding any enzyme, resulting in the formation of 2-pyrrolidone, valerolactam and caprolactam, respectively (FIGS. 6, 7, and 11).

Accordingly, in another aspect of the present disclosure, it provides a method for preparing a lactam from an omega-amino acid, in which the method includes the steps of: (a) mixing a beta-alanine coenzyme A transferase with a reaction solution containing the omega-amino acid and then reacting to prepare an omega-amino acyl-CoA; and (b) preparing the lactam by forming a ring structure of the produced omega-amino acyl-CoA.

In the present disclosure, the gene encoding the beta-alanine coenzyme A transferase may be, but not limited to, characterized to be an act derived from *Clostridium propionicum*.

In the present disclosure, the lactam may be any chemical substance characterized in that it has a heterocyclic ring structure and has an amide bond in the ring, but may be preferably characterized to be one selected from the group consisting of propiolactam, 2-pyrrolidone, valerolactam, caprolactam, heptanolactam, octanolactam, nonanolactam, decanolactam, undecanolactam, and dodecanolactam.

In still another aspect of the present disclosure, it provides a method for preparing an omega-amino acyl-CoA from an omega-amino acid using the recombinant microorganism into which a beta-alanine coenzyme A transferase gene is introduced, in which the method includes the steps of: (a) culturing the recombinant microorganism to produce the omega-amino acyl-CoA; (b) recovering the produced omega-amino acyl-CoA.

In the present disclosure, the step of recovering the produced omega-amino acyl-CoA may be, but not limited to, characterized by including the steps of disrupting cells to obtain a mixture containing omega-amino acyl-CoA; and recovering the omega-amino acyl-CoA through a purification process.

The cell disruption of the present disclosure may be performed by various methods known to those skilled in the art, and is preferably, but not limited to, characterized by being performed using a sonic wave process. The purification process may be but not limited to, characterized by being performed using a chromatogram.

In the present disclosure, the step of recovering the produced omega-amino acyl-CoA is characterized by further including a step of immobilizing the cells before disrupting the cells, or a step of treating the compounds to prevent the formation of a ring of the omega-amino acyl-CoA.

In yet another aspect of the present disclosure, it relates to a method for preparing an omega-amino acyl-CoA from an omega-amino acid, in which the method includes the step of mixing a beta-alanine coenzyme A transferase in a reaction solution containing the omega-amino acid and then reacting to prepare the omega-amino acyl-CoA.

In the present disclosure, the gene encoding the beta-alanine coenzyme A transferase may be, but not limited to, characterized to be an act derived from *Clostridium propionicum*.

In the present disclosure, the omega-amino acid may be any chemical substance characterized in that it has an amine and a carboxylic acid functional group at the same time, but may be preferably characterized to be one selected from the group consisting of beta-alanine, gamma-aminobutyric acid (GABA), 5-aminovaleric acid (5AVA), 6-aminocaproic acid (6ACA), 7-aminoheptanoic acid (7AHA), 8-aminooctanoic acid, 9-aminononanoic acid, 10-aminodecanoic acid, 11-aminoundecanoic acid, and 12-aminododecanoic acid.

In the present disclosure, the term "vector" means a DNA product containing a DNA sequence operably linked to a suitable regulatory sequence capable of expressing DNA within an appropriate host. The vector may be a plasmid, a phage particle, or simply a potential genome insertion. Once transformed into the appropriate host, the vector may replicate and function independently of the host genome, or, in some cases, integrate into the genome itself. As the plasmid is the most commonly used form of the current vector, the terms "plasmid" and "vector" are sometimes used interchangeably in the context of the present disclosure. However, the present disclosure includes other forms of vectors having functions equivalent to those known or known in the art. Typical expression vectors for mammalian cell culture expression are based on, for example, pRK5 (EP 307,247), pSV16B (WO 91/08291), and pVL1392 (Pharmingen).

The phase "expression regulatory sequence" means a DNA sequence that is essential for the expression of a coding sequence operably linked to a particular host organism. Such regulatory sequence includes a promoter for conducting transcription, any operator sequences for controlling such transcription, a sequence encoding suitable an mRNA ribosome binding site, and a sequence controlling the termination of transcription and translation. For example, a regulatory sequence suitable for a prokaryotic cell includes a promoter, any operator sequences, and a ribosome binding site. The eukaryotic cell includes a promoter, a polyadenylation signal, and an enhancer. The most influential factor on the expression level of the gene in the plasmid is a promoter. As a promoter for high expression, an SRα promoter, a cytomegalovirus-derived promoter, etc. are preferably used.

In order to express the DNA sequence of the present disclosure, any of a wide variety of expression regulatory sequences may be used in the vector. Examples of useful expression regulatory sequences include, for example, early and late promoters of SV40 or adenovirus, lac system, trp system, TAC or TRC system, T3 and T7 promoters, major operator and promoter regions of phage lambda, a control region of fd coding protein, a promoter for 3-phosphoglycerate kinase or other glycolytic enzymes, a promoter of the phosphatase, such as Pho5, a promoter of yeast alpha-mating system and a prokaryotic or eukaryotic cell or constitution known to control the expression of the genes of these viruses and other sequences of induction, and combinations thereof. T7 RNA polymerase promoter Φ10 can be useful for expressing protein NSP in *Escherichia coli*.

A nucleic acid is "operably linked" when placed in a functional relationship with another nucleic acid sequence. This may be the gene and regulatory sequence(s) that are linked in such a way that it is capable of gene expression when an appropriate molecule (e.g., Transcriptional activator protein) is combined with the regulatory sequence (s). For example, DNA for a pre-sequence or secretory leader is operably linked to DNA for a polypeptide when expressed as a pre-protein participating in the secretion of the polypeptide; the promoter or enhancer is operably linked to a coding sequence when it affects the transcription of the sequence; the ribosome binding site is operably linked to a coding sequence when it affects the transcription of the sequence; or the ribosome binding site is operably linked to a coding sequence when positioned in an easy translation. Generally, "operably linked" means that the linked DNA sequence is in contact and, in the case of a secretory leader, is in contact and present in the reading frame. However, the enhancer need not be in contact. The linkage of these sequences is carried out by ligation (connection) at the convenient restriction enzyme site. If such sites do not exist, a synthetic oligonucleotide adapter or linker according to conventional methods is used.

As used herein, the term "expression vector" is usually a recombinant carrier into which a fragment of hetero DNA is inserted, and generally refers to a fragment of double-stranded DNA. Herein, the hetero DNA means a hetero DNA that is not naturally found in the host cell. Once the expression vector is in a host cell, it can replicate independently of the host chromosome DNA and several copies of the vector and its inserted (hetero) DNA can be generated.

As is well known in the art, in order to increase the expression level of a transfected gene in a host cell, the corresponding gene must be operably linked to transcription and translation expression regulatory sequences that function in a selected expression host. Preferably, the expression regulatory sequence and the corresponding gene are contained within an expression vector containing a bacterial selection marker and a replication origin. If the expression host is a eukaryotic cell, the expression vector should further include a useful expression marker in the eukaryotic expression host.

A host cell transformed or transfected with the above-described expression vector constitutes another aspect of the present disclosure. As used herein, the term "Transformation" means introducing DNA into a host to make the DNA replicable as an extrachromosomal factor or by chromosomal integration. The term "transfection" as used herein means that an expression vector is accepted by a host cell whether or not any coding sequence is actually expressed.

The host cell of the present disclosure may be a prokaryotic or eukaryotic cell. In addition, a host having high efficiency of introduction of DNA and high efficiency of expression of the introduced DNA is usually used. Known eukaryotic and prokaryotic hosts such as *Escherichia coli, Pseudomonas, Bacillus, Streptomyces*, fungi, and yeast, insect cells such as *Spodoptera frugiperda* (SF9), animal cells such as CHO and mouse cells, African green monkey cells such as COS 1, COS 7, BSC 1, BSC 40 and BMT 10, and tissue-cultured human cells are examples of host cells that can be used. When the cDNA encoding the NSP protein of the present disclosure is cloned, it is preferable that the animal cell is used as a host. In the case of using COS cells, since SV40 large T antigen is expressed in COS cells, the plasmid having SV40 replication origin is present as a multiple copy of episomes in the cells, and higher expression can be expected than the usual. The introduced DNA sequence may be obtained from the same species as the host cell or may be obtained from a different species from the host cell, or it may be a hybrid DNA sequence including any heterologous or homologous DNA.

Further, it should be understood that not all vectors and expression regulatory sequences function equally well in expressing the DNA sequences of the present disclosure. Likewise, not all hosts function identically for the same expression system. However, those skilled in the art will be able to make appropriate selections among a variety of vectors, expression regulatory sequences, and hosts without undue experimentation and without departing from the scope of the present disclosure. For example, in selecting a vector, the host should be considered because the vector must be replicated within it. The number of copies of the vector, the ability to control the number of copies, and the expression of other proteins encoded by the corresponding vector, such as antibiotic markers, must also be considered. In selecting expression regulatory sequences, a number of factors must be considered. For example, the relative strength of the sequence, controllability and compatibility with the DNA sequences of the present disclosure, particularly regarding possible secondary structures, should be considered. The single cell host should be selected by considering factors such as a selected vector, the toxicity of the product encoded by the DNA sequence of the present disclosure, the secretion characteristics, the ability to fold the protein correctly, the culture and fermentation requirements, the easiness of refining the product encoded by the DNA sequence of the present disclosure from the host. Within the scope of these variables, one skilled in the art can select various vector/expression regulatory sequences/host combinations that can express the DNA sequences of the present disclosure in fermentation or large animal cultures. As a screening method for cloning cDNA of NSP protein by expression cloning, a binding method, a panning method, a film emulsion method, or the like can be applied.

As the definition of the present disclosure, "substantially pure" means that the polypeptide and the DNA sequence encoding the polypeptide according to the present disclosure do not substantially include other proteins derived from bacteria.

Host cells for expressing recombinant proteins are widely used for prokaryotic cells such as *Escherichia coli* and *Bacillus subtillis*, which are capable of culturing high-density cells in a short period, are easy to manipulate genes, and are well-characterized for their genetic and physiological characteristics. However, in order to solve the problems of post-translational modification, secretion process, active three-dimensional structure, and active state of proteins, because recently cells ranging from single cell eukaryotic cells to higher organisms such as yeast series (*Pichia pastoris, Saccharomyces cerevisiae, Hansenula polymorpha*, etc.), filamentous fungi, insect cells, plant cells, and mammalian cells are used as a host cell for the production of recombinant protein, the use of other host cells as well as *Escherichia coli* which is exemplified in the examples is readily applicable to those of ordinary skill in the art.

Hereinafter, the present disclosure will be described in more detail with reference to examples. It is to be understood by those skilled in the art that these examples are only for illustrating the present disclosure and that the scope of the present disclosure is not construed as being limited by these examples.

Example 1. Confirmation of In Vitro Activity of Beta-Alanine Coenzyme A Transferase 1-1: Preparation of pET30α his_Act Vector The amino acid sequence of the beta-alanine coenzyme A transferase derived from *Clostridium propionicum* strain and the nucleotide sequence of the act gene encoding it are shown in SEQ ID NOS: 2 and 1, respectively.

PCR was performed using the chromosomal DNA of *Clostridium propionicum* strain as a template and the primers of SEQ ID NOS: 3 and 4 to prepare a his_act gene fragment for encoding a beta-alanine coenzyme A having a his-tag at the N terminus.

```
[SEQ ID NO: 3] ckphisact (NdeI, F):
5'-AGACAGCATATGCACCATCATCATCATCATAAAAGACCCTTGGAAGG
TATTCG-3'

[SEQ ID NO: 4] ckpact (SalI, R):
5'-AGACAGGTCGACTTAGATGACATTTTTCTCTTCCAGTGA-3'
```

Figure 2:
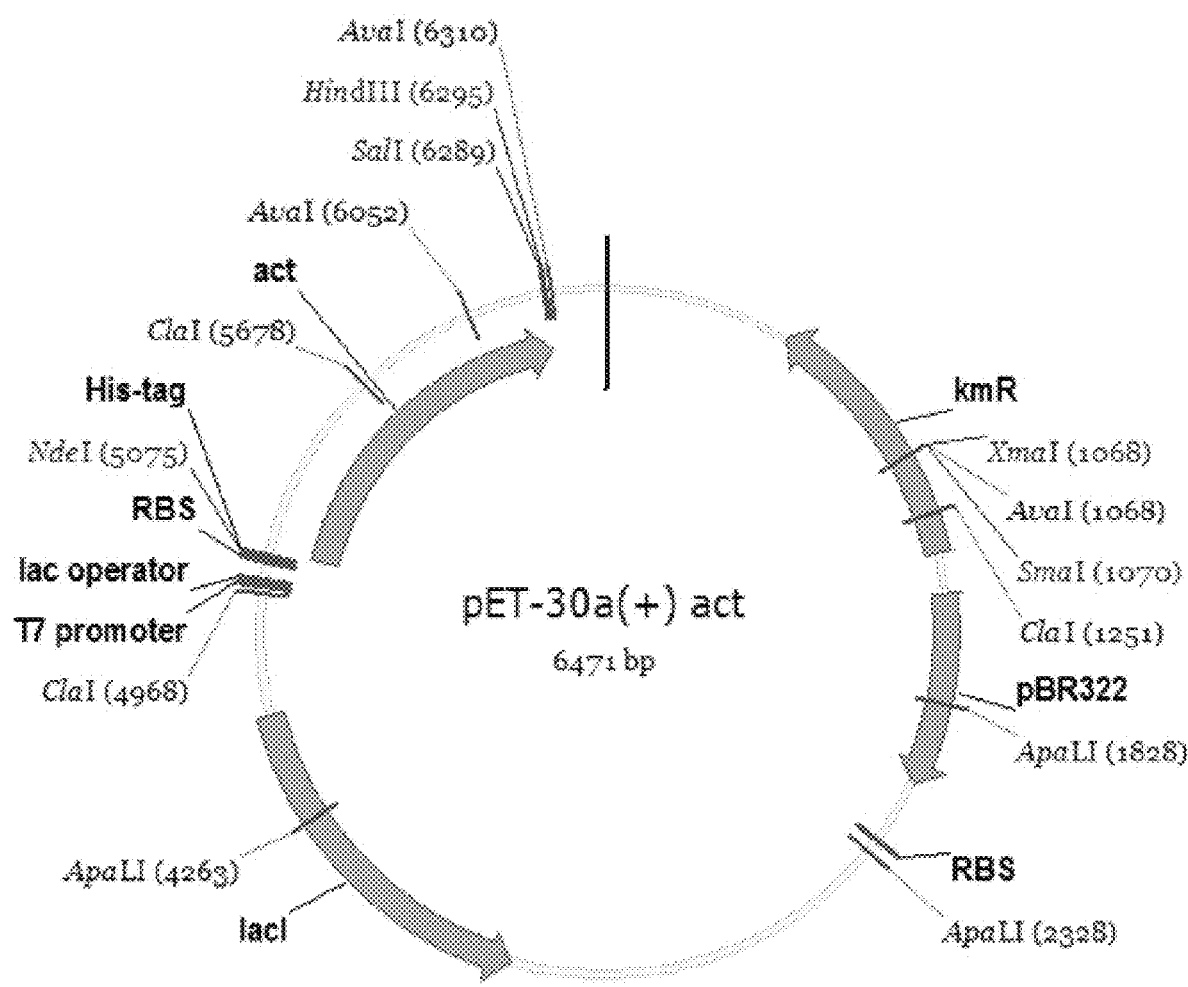
FIG. 2 shows a plasmid overexpressing pET30α his-act in which a his-tagged act gene is inserted for the purification of a beta-alanine coenzyme A transferase.

Next, the his_act fragment and the pET30α plasmid were treated with restriction enzymes (NdeI and SalI), then treated with T4 DNA ligase so that the his_act fragment digested with restriction enzymes and the pET30α plasmid were combined to prepare a recombinant plasmid pET30α_his_act (See FIG. 2).

1-2: Purification of Beta-Alanine Coenzyme A Transferase

For purification of the beta-alanine coenzyme A transferase, the plasmid pETa_his_act obtained in Example 1-1 was introduced into *E. coli* BL21 (DE3) (F-ompT hsdSB (rB- mB-) gal dcm (DE3) a prophage carrying the T7 RNA polymerase gene) (New England Biolabs, USA).

After the early incubation that the transformed strains were inoculated into 10 mL LB liquid medium (10 g/L tryptone, 5 g/L yeast extract, and 10 g/L NaCl) containing 25 mg/L of kanamycin and continuously shaken at 200 rpm at 37° C., the cells were inoculated 1% in 200 ml of the medium described above and incubated at 37° C. with shaking constantly at 200 rpm. Then, 1 mM IPTG was added to induce his_act expression when the optical density (OD) measured at a wavelength of 600 nm was 0.4 in a spectrophotometer.

After 4 hours of expression induction, the culture was treated with 3000 rpm at 4° C. for 10 minutes in a centrifuge (Hanil Science Industrial, Korea) to isolate microorganisms and remove a supernatant. The isolated microorganisms were placed in 40 mL of an equilibrium buffer (50 mM $Na_3PO_4$, 300 mM NaCl, pH 7.0), then were dissolved by way of pulsing for 5 seconds at 30% intensity and standing for 5 seconds using a cell sonicator (Sonics & Materials, Inc., USA) for 2 hours, and then were centrifuged at 13200 rpm at 4° C. for 10 minutes to remove cell debris and then obtain a cell lysate.

The cell lysate was purified with a 0.45 μm filter, and the his-tagged beta-alanine coenzyme A transferase was isolated using Talon resin (Clontech Laboratories, Inc., USA). Isolation of beta-alanine coenzyme A transferase attached on Talon resin was performed using equilibrium buffers containing 7.5, 15, 30, 45, 60, 90, 120, and 150 mM imidazole, respectively. Thereafter, the samples that the whole cell lysate, the protein solution passed through the talon resins, and the protein solution obtained with each concentration of imidazole were mixed with 5× Laemmli sample buffer solution (LPS Solution, Korea) were separated using 12% SDS-PAGE and stained with Coomassie brilliant blue R250 (Bio-Rad, USA) solution (See FIG. 3). As a result, the beta-alanine coenzyme A transferase purified to the highest purity 120 mM was used.

1-3: Enzyme Assay of Beta-Alanine Coenzyme A Transferase

Enzyme assay was performed in 50 mM potassium phosphate buffer (pH 7.5). Substrates and enzymes required for the enzyme assay were added as follows. 10 mM GABA, 6ACA or 7AHA, 1 mM acetyl-CoA, and 2.5 µg purified beta-alanine coenzyme A transferase were added and reacted at 30° C. for 2 hours. To isolate the only coenzyme A derivatives from the enzyme assay mixture, the following protocols were used with an OASIS HLB SPE cartridge (Waters, USA).

The first cartridge was poured with 1 mL of methanol, followed by 2 mL of 0.15% TCA solution. After that, a mixture of enzyme assay was flowed and then 1 mL of 0.15% TCA solution again was flowed. Finally, 1 mL of a solution of methanol and $NH_4OH$ in a 99:1 volume ratio was flowed to obtain purified coenzyme A derivatives. The solvent was blown using a vacuum centrifuge, and the sample was stored at −24° C.

The samples were dissolved in distilled water just before analysis using HPLC-MS (Mass spectrometers: LC/MSD VL, Agilent, USA, HPLC: Agilent, USA) or HPLC-MS/MS (Mass spectrometers: API3200QTRAP, SCIEX, USA, HPLC: Shimadzu, Japan), and then the coenzyme A derivatives were analyzed. It was analyzed in the positive mode using HPLC-MS/MS in the case of the enzyme assay mixture using GABA and 6ACA as the substrate, and it was analyzed in the negative mode using the HPLC-MS in the case of the essay mixture using 7AHA as the substrate.

As a result, a primary MS analysis of the enzyme assay mixture using GABA as a substrate revealed a peak at 852.2, which is similar to the expected m/z value of 853 of GABA coenzyme A. This peak was fragmented with secondary MS and the analysis was carried out. As a result, peaks were confirmed at 243.1, 345.5 and 428.1, which are similar to the expected peaks m/z=244, 346, and 428, respectively (See FIG. 4). Further, a primary MS analysis of the enzyme assay mixture using 6ACA as a substrate revealed a peak at 881.3, which is similar to the expected m/z value of 881 of GABA coenzyme A. This peak was fragmented with secondary MS and the analysis was carried out. As a result, peaks were confirmed at 272.2, 374.3, and 428.2, which are similar to the expected peaks m/z=272, 374, and 428, respectively (See FIG. 5). Further, in the case of the enzyme assay mixture proceeding using 7AHA as a substrate, it was confirmed that a new CoA derivative peak appeared at t=9.844 minutes and had the same value as the expected m/z value of 893.2 of 7AHA coenzyme A (See FIG. 10).

From these results, it was confirmed that beta-alanine coenzyme A transferase successfully converted GABA, 6ACA, and 7AHA to GABA coenzyme A, 6ACA coenzyme A, and 7AHA coenzyme A, respectively, according to the present disclosure.

Example 2. Confirmation of Production of 2-Pyrrolidone, Valerolactam, and Caprolactam In Vitro GABA coenzyme A, 5AVA coenzyme A, and 6ACA coenzyme A were prepared by proceeding enzyme assay using the described method in Example 1-3. The resulting GABA coenzyme A, 5AVA coenzyme A, and 6ACA coenzyme A were allowed to stand at 37° C. for 48 hours without any treatment and then analyzed using HPLC-MS to confirm the production of 2-pyrrolidone, valerolactam, and caprolactam.

As a result, a standard 2-pyrrolidone reagent (Sigma-Aldrich, USA) was analyzed by HPLC-MS to detect the peak of 2-pyrrolidone at 6.352 minutes, and this peak was analyzed by MS analysis to confirm peaks showed at m/z=86.1 and 108.1. As a control, the assay mixture containing no beta-alanine coenzyme A transferase, i.e., not producing GABA coenzyme A, was analyzed. As a result, it was confirmed that no peak appeared in the 6-minute band.

In the assay mixture sample in which a beta-alanine coenzyme A transferase was added to prepare GABA coenzyme A, a peak was detected at 6.348 minutes which is similar to that of the standard 2-pyrrolidone reagent. MS analysis of the peak showed that peaks were detected at m/z=86.0 and 108.0 which are similar to that of the standard 2-pyrrolidone reagent (See FIG. 6). Further, as an analysis result of the standard valerolactam reagent (Sigma-Aldrich, USA) by HPLC-MS, a peak of valerolactam was detected at 8.098 minutes. MS analysis of the peak showed that a peak appeared at m/z=100.1.

In the assay mixture sample in which a beta-alanine coenzyme A transferase added to prepare 5AVA coenzyme A transferase, a peak was detected at 8.092 minutes which is similar to that of the standard valerolactam reagent. MS analysis of the peak showed that a peak was detected at m/z=100.1 which is similar to that of the standard valerolactam reagent (See FIG. 11). Analysis of the standard caprolactam reagent (Sigma-Aldrich, USA) by HPLC-MS showed that a peak of caprolactam was detected at 9.395 minutes. MS analysis of the peak showed that peaks appeared at m/z=114.1 and 136.0, respectively.

In the case of the assay mixture in which 6ACA coenzyme A was not produced because a beta-alanine coenzyme A transferase did not enter into, as the above logic, no peak was detected in the 9-minute band. In the case of the assay mixture sample in which beta-alanine coenzyme A transferase was added to prepare 6ACA coenzyme A, a peak was detected at 9.469 minutes, similar to that of the standard caprolactam reagent. MS analysis of this peak confirmed that peaks were detected at m/z=114.1 and 136.0, similar to that of the standard caprolactam reagent (See FIG. 7).

From these results, it was confirmed that GABA coenzyme A, 5AVA coenzyme A, and 6ACA coenzyme A prepared using beta-alanine coenzyme A transferase according to the present disclosure are converted to 2-pyrrolidone, valerolactam, and caprolactam, respectively, without the help of enzymes.

Example 3: Production of Lactam from Omega-Amino Acid Using Recombinant Microorganism 3-1: Preparation of pTac15k_Act Vector An act gene fragment encoding a beta-alanine coenzyme A was prepared by performing PCR using primers of SEQ ID NOS: 5 and 6 and taking the chromosomal DNA of *Clostridium propionicum* strain as a template.

[SEQ ID NO: 5] ckpact (EcoRI, F):
5'-AGACAGGAATTCATGAAAAGACCCTTGGAAGGTATT-3'

[SEQ ID NO: 6] ckpact (SacI, R):
5'-AGACAGGTCGACTTAGATGACATTTTTCTCTTCCAGTG-3'

Figure 8:
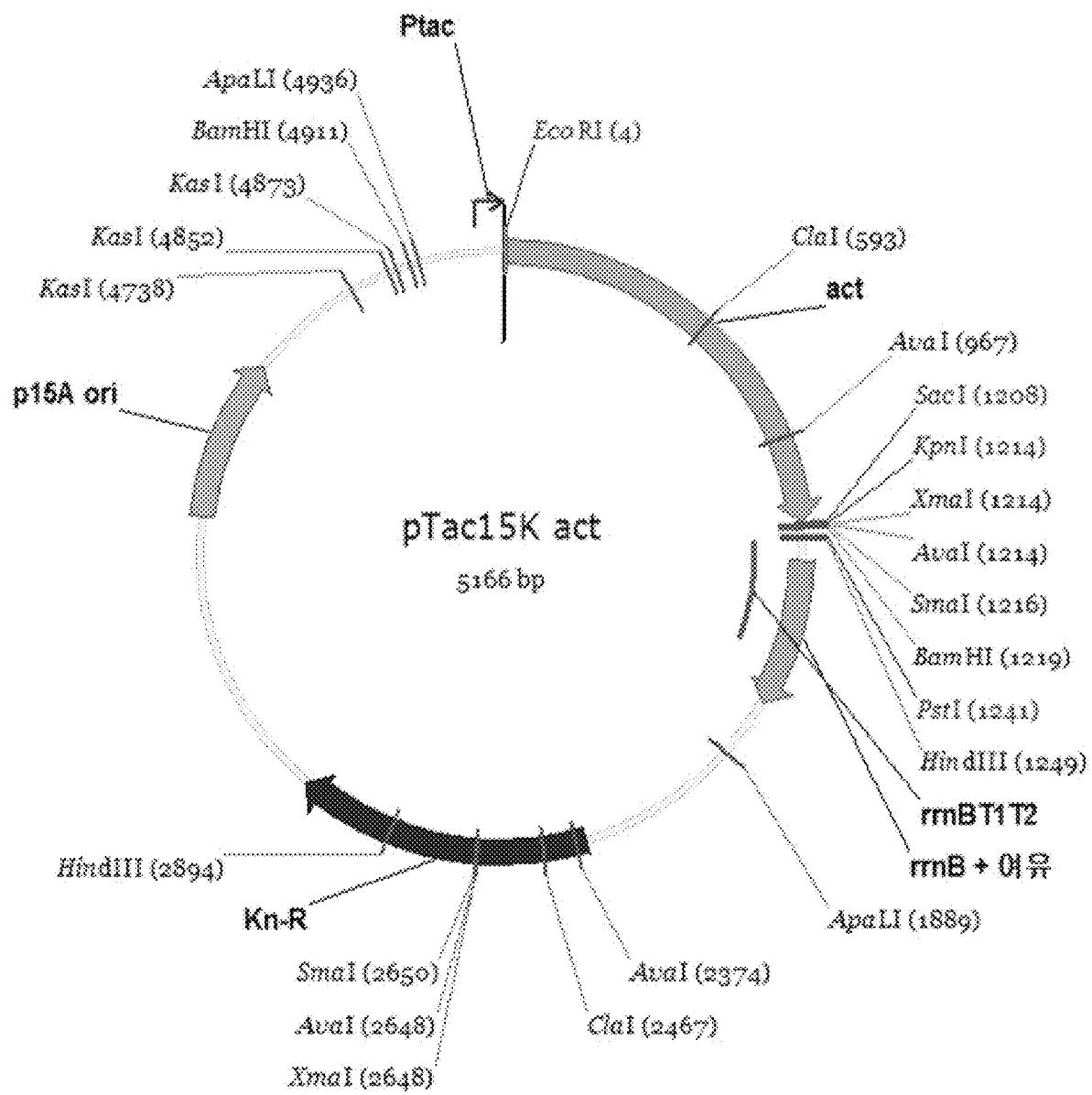
FIG. 8 shows a pTac15k_act plasmid prepared for the expression of a beta-alanine coenzyme A transferase in a microorganism, in which an act gene is inserted.

Next, pTac15k (Hiszczyn' ska-Sawicka and Kur, 1997) plasmid, which progresses strong gene expression of the act fragment and tac promoter, was treated with restriction enzymes (EcoRI and SacI), then treated with T4 DNA ligase, so that the restriction enzyme-cleaved act fragment and the pTac15k plasmid were ligated to prepare a recombinant plasmid pTac15k_act (See FIG. 8).

Figure 13:
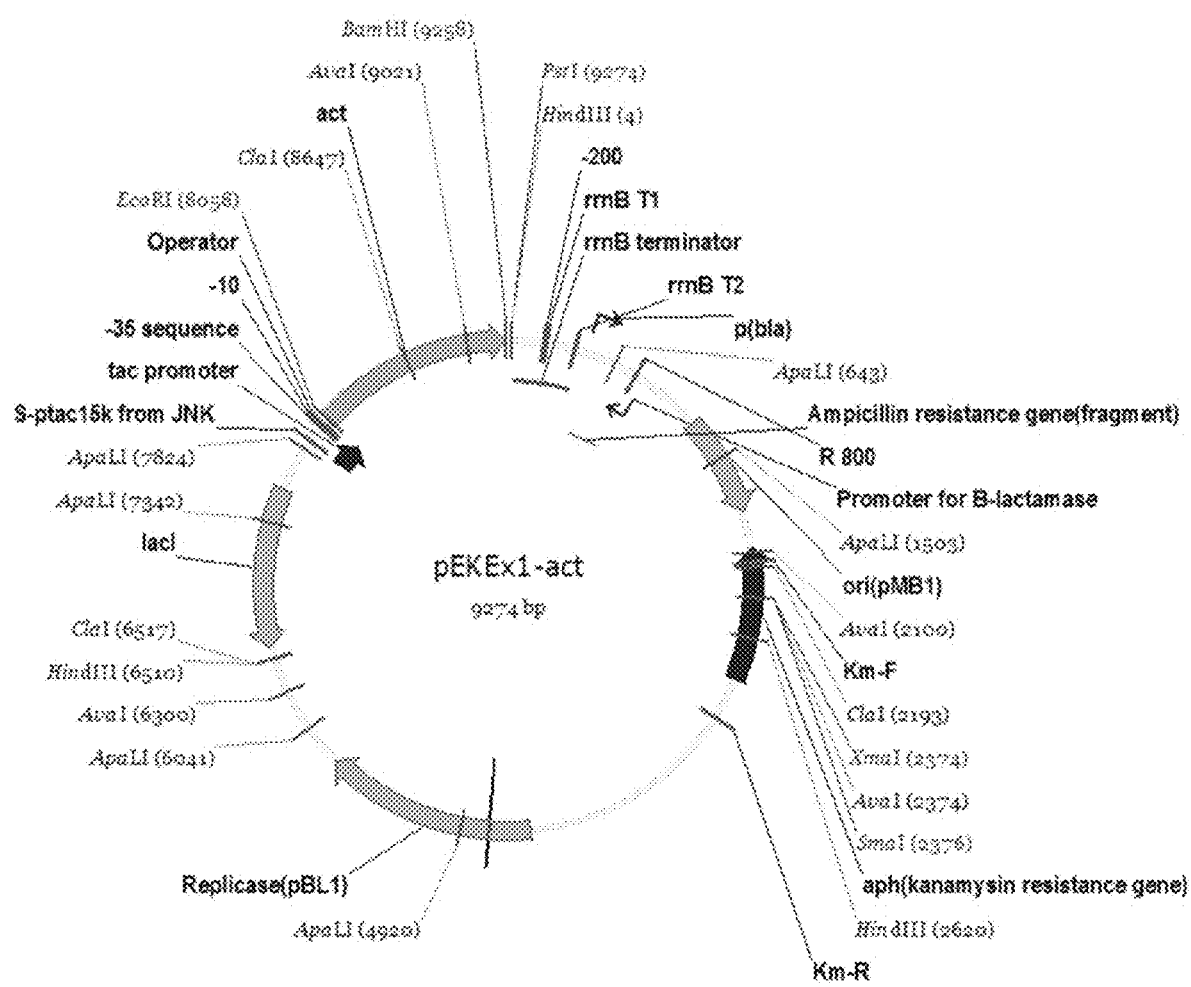
FIG. 13 shows a pEKEx1_act plasmid prepared for the expression of a beta-alanine coenzyme A transferase in a microorganism, in which an act gene is inserted.

3-2: Preparation of pEKEx1_Act Vector pEKEx1 (Eikmanns et al., Gene. 102, 93-98, 1991) plasmid carrying the strong gene expression of the act fragment prepared in Example 3-1 and tac promoter, was treated with restriction enzymes (EcoRI and BamHI), then treated with T4 DNA ligase, so that the restriction enzyme-cleaved act fragment and the pEKEx1 plasmid were ligated to prepare a recombinant plasmid pEKEx_act (See FIG. 13).

3-3: Preparation of pEKEx1_gadB Vector

Using the chromosomal DNA of the *Escherichia coli* strain as a template, PCR was performed with the primers of SEQ ID NOs: 8 and 9 to prepare a gadB gene fragment encoding glutamic acid decarboxylase.

[SEQ ID NO: 7] ecjgadB (BamHI, RBS, F):
5'-AGACAGGGATCCTTTCACACAGGAAACAATGGATAAGAAGCAAGTAACGGATT-3'

[SEQ ID NO: 8] ecjgadB (SalI, R):
5'-AGACAGGTCGACTCAGGTATGTTTAAAGCTGTTCTGTT-3'

Figure 14:
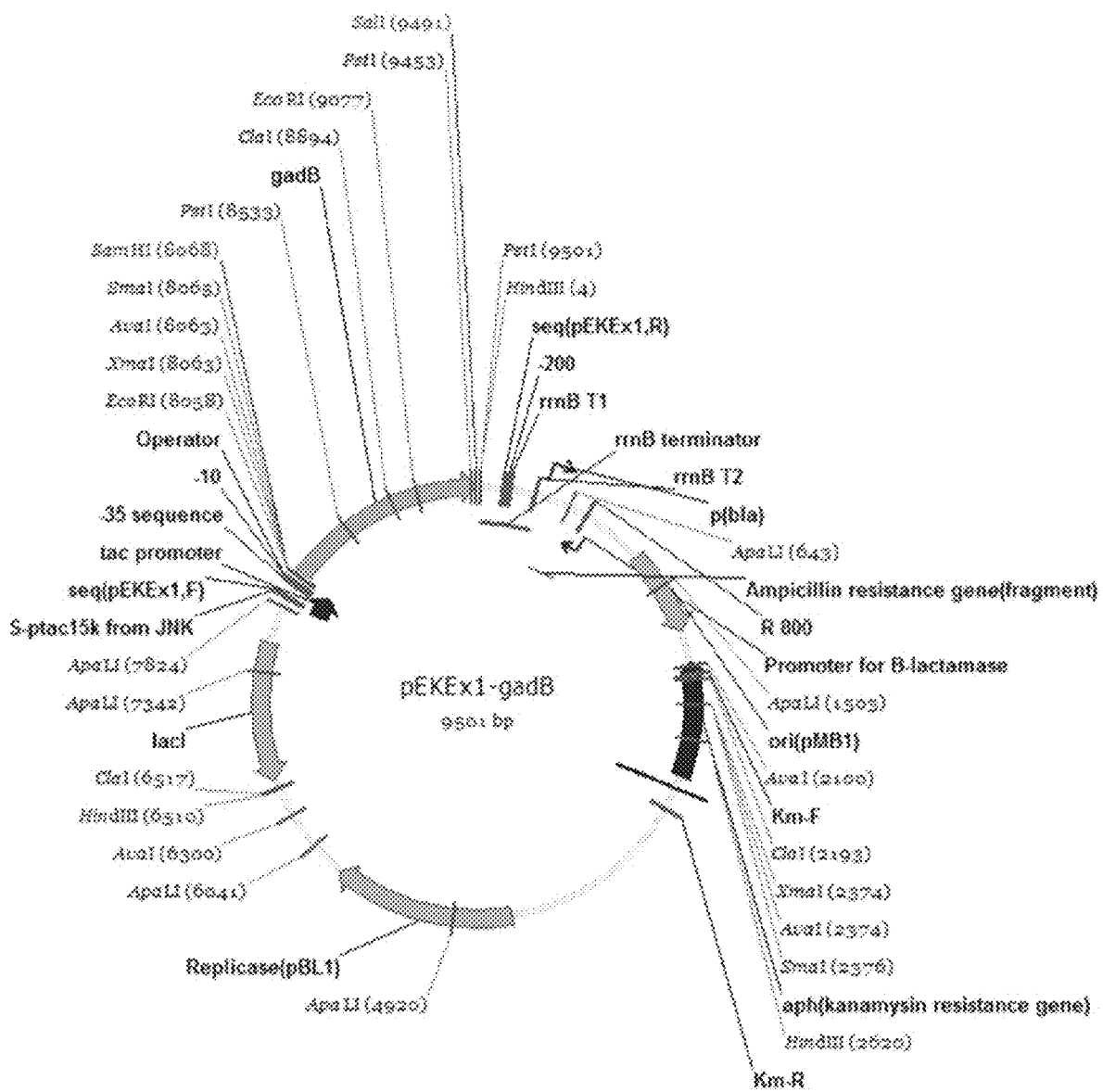
FIG. 14 shows a pEKEx1_gadB plasmid prepared for the expression of a glutamic acid decarboxylase in a microorganism, in which a gadB gene is inserted.

Next, pEKEx1 (Eikmanns et al., Gene. 102, 93-98, 1991) plasmid carrying strong gene expression of gadB fragment and tac promoter was treated with restriction enzymes (BamHI and SalI), then treated with T4 DNA ligase, so that the restriction enzyme-cleaved gadB fragment and the pEKEx1 plasmid were ligated to prepare a recombinant plasmid pEKEx_gadB (See FIG. 14).

3-4: Preparation of pEKEx1_Act_gadB Vector

Figure 15:
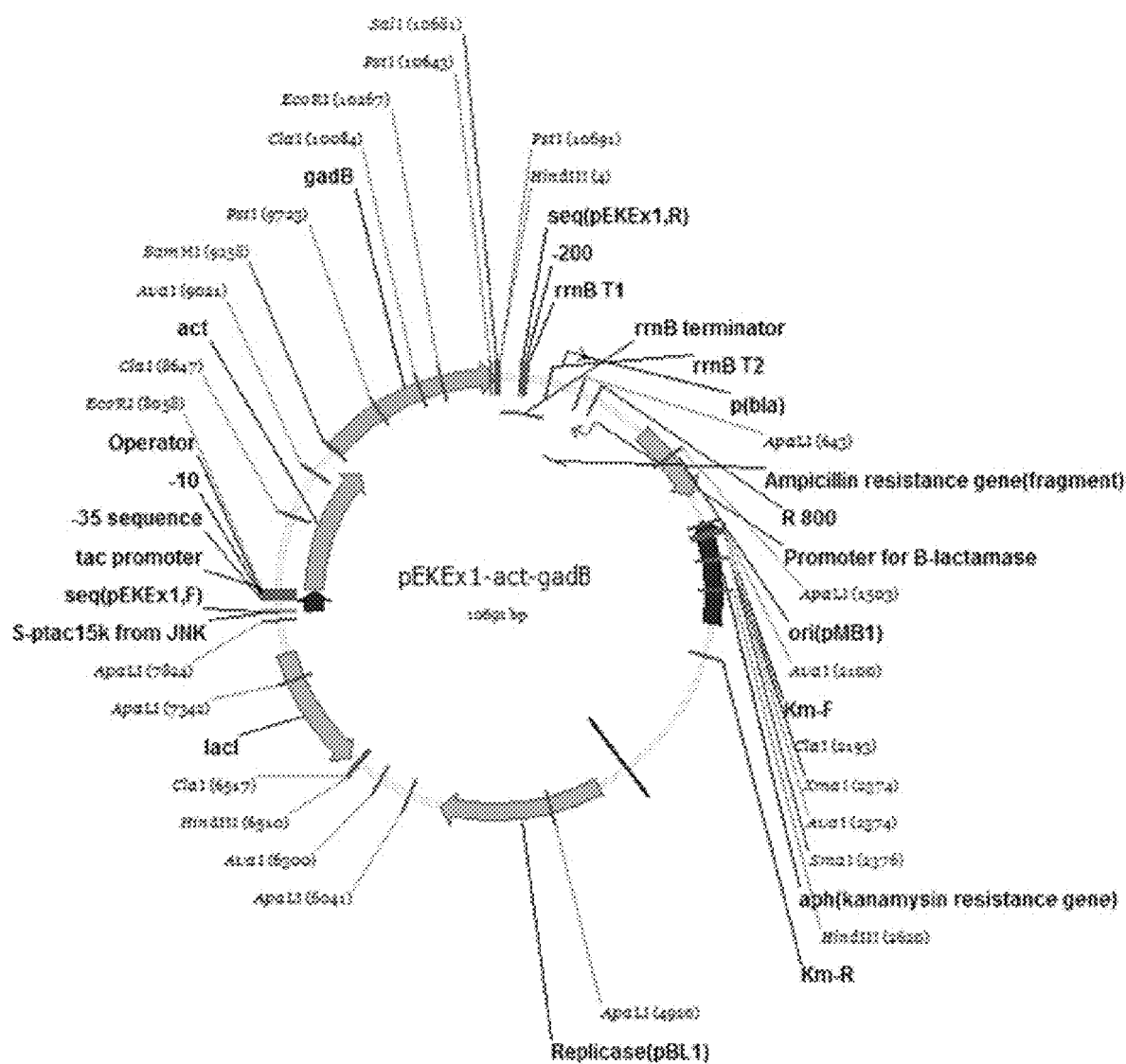
FIG. 15 shows a pEKEx1_act_gadB plasmid prepared for the expression of a beta-alanine coenzyme A transferase and a glutamic acid decarboxylase in a microorganism, in which act and gadB gene are inserted.

The pEKEx1-act plasmid prepared in Example 3-2 and the gadB fragment prepared in Example 3-2 were treated with restriction enzymes (BamHI and SalI), then treated with T4 DNA ligase so that the restriction enzyme-cleaved gadB fragment and the pEKEx1_act plasmid were ligated to prepare a recombinant plasmid pEKEx_act_gadB (See FIG. 15).

3-5: Production of Recombinant Microorganism

The pTac15k_act plasmid prepared in Example 3-1 was introduced into *Escherichia coli* WL3110 (Lee et al., *Mol. Syst. Biol.* 3: 149 2007) so that the act gene encoding the beta-alanine coenzyme A gene was expressed in the microorganism, thereby preparing a recombinant microorganism (WL3110/pTac15k-act), and *Escherichia coli* (WL3110/pTac15k) into which pTac15k, an empty vector, was introduced, was used as a control strain.

Further, in order to detect the possibility of production in various carbon sources, the pTac15k_act plasmid prepared in Example 3-1 was introduced into *Escherichia coli* XQ56/pKE112-davAB (Park et al., *Metab. Eng.* 16:42-47 2013) so that the act gene encoding the beta-alanine coenzyme A gene was expressed in the microorganism, thereby preparing a recombinant microorganism (XQ56/pKE112-davAB/pTac15k-act), and *Escherichia coli* (XQ56/pKE112-davAB/pTac15k) into which pTac15k, an empty vector, was introduced, was used as a control strain.

Further, in order to detect the possibility of production in various carbon sources, pEKEx1_act_gadB plasmid prepared in Example 3-4 was introduced into the wild-type *Corynebacterium glutamicum* (ATCC 13032) so that the gadB gene encoding the glutamic acid decarboxylase gene for biosynthesis of GABA and the act gene encoding the beta-alanine coenzyme A gene were expressed in the microorganism, thereby preparing a recombinant microorganism (ATCC 13032/pEKEx1_act_gadB). *Corynebacterium glutamicum* (ATCC 13032/pEKEx1_gadB), into which the pEKEx1_gadB plasmid was introduced, was used as a control strain. The pEKEx1_gadB plasmid was prepared in Example 3-3 and expressed only gadB gene.

3-6: Confirmation of Production of 2-Pyrrolidone from GABA Using Recombinant Microorganism The recombinant microorganism (WL3110/pTac15k-act) prepared in Example 3-5 was inoculated into 10 mL of LB medium, pre-cultured at 37° C. for 8 hours, and 1.5 mL of the pre-cultured medium was inoculated in 50 mL modified MR-1 medium of a 350 mL flask and cultured.

The composition of the modified MR-1 medium (pH 7.0) contained 10 g glucose, 5 g GABA, 9 g $(NH_4)_2SO_4$, 6.67 g $KH_2PO_4$, 4.0 g $(NH_4)_2HPO_4$, 0.8 g citric acid, 0.8 g $MgSO_4 \cdot 7H_2O$, 0.01 g $CaCl_2 \cdot 2H_2O$, 5 mL trace metal solution (10 g $FeSO_4 \cdot 7H_2O$, 2.2 g $ZnSO_4 \cdot 4H_2O$, 0.58 g $MnSO_4 \cdot 4H_2O$, 1 g $CuSO_4 \cdot 5H_2O$, 0.1 g $(NH_4)_6Mo_7O_{24} \cdot 4H_2O$, 0.02 g $Na_2B_4O_7 \cdot 10H_2O$ per 1 liter distilled water) per 1 liter distilled water. GABA was supplied as a carbon source in the above composition. The culture was carried out in a shaking incubator (jSR, Korea) operating at 37° C. and 200 rpm for 48 hours. After the culture was completed, the culture solution was centrifuged at 13,200 rpm for 10 minutes, and only the supernatant was collected and subjected to HPLC-MS analysis to confirm the production of 2-pyrrolidone.

As a result, as shown in Table 1, it was confirmed that the recombinant microorganism according to the present disclosure produced 193.78 mg/L of 2-pyrrolidone, whereas the 2-pyrrolidone was not produced at all in the recombinant microorganism in which an empty vector was transformed.

From these results, it was confirmed that the recombinant microorganism according to the present disclosure successfully produced 2-pyrrolidone using GABA as a carbon source.

TABLE 1

| Production amount (mg/L) of 2-pyrrolidone of recombinant microorganism | |
|---|---|
| Strain | Production amount of 2-pyrooidone(mg/L) |
| WL3110/pTac15k | 0 |
| WL3110/pTac15k-act | 193.78 |

3-7: Confirmation of Production of Valerolactam from 5AVA Using Recombinant Microorganism The recombinant microorganism (WL3110/pTac15k-act) prepared in Example 3-5 was inoculated into 10 mL of LB medium, pre-cultured at 37° C. for 8 hours, and 1.5 mL of the pre-cultured medium was inoculated in the 50 mL modified MR-2 medium of a 350 mL flask and cultured.

The composition of the modified MR-2 medium (pH 7.0) contained 10 g glucose, 5 g 5AVA, 9 g $(NH_4)_2SO_4$, 6.67 g $KH_2PO_4$, 4.0 g $(NH_4)_2HPO_4$, 0.8 g citric acid, 0.8 g $MgSO_4 \cdot 7H_2O$, 0.01 g $CaCl_2 \cdot 2H_2O$, 5 mL trace metal solution (10 g $FeSO_4.7H_2O$, 2.2 g $ZnSO_4.4H_2O$, 0.58 g $MnSO_4.4H_2O$, 1 g $CuSO_4.5H_2O$, 0.1 g $(NH_4)_6Mo_7O_{24}.4H_2O$, 0.02 g $Na_2B_4O_7.10H_2O$ per 1 liter distilled water) per 1 liter distilled water. 5AVA was supplied as a carbon source in the above composition. The culture was carried out in a shaking incubator (jSR, Korea) operating at 37° C. and 200 rpm for 48 hours. After the culture was completed, the culture solution was centrifuged at 13,200 rpm for 10 minutes, and only the supernatant was collected and subjected to HPLC-MS analysis to confirm the production of valerolactam.

As a result, as shown in Table 2, it was confirmed that the recombinant microorganism according to the present disclosure produced 592.68 mg/L of valerolactam.

From these results, it was confirmed that the recombinant microorganism according to the present disclosure successfully produced valerolactam using 5AVA as a carbon source.

TABLE 2

Production amount (mg/L) of valerolactam of recombinant microorganism

| Strain | Production amount of valerolactam (mg/L) |
|---|---|
| WL3110/pTac15k-act | 592.68 |

Example 4: Production of Lactam from Other Carbon Source Using Recombinant Microorganism 4-1: Confirmation of Production of 2-Pyrrolidone from Glutamic Acid Using Recombinant Microorganism The recombinant microorganism (WL3110/pTac15k-act) prepared in Example 3-5 was inoculated into 10 mL of LB medium, pre-cultured at 37° C. for 8 hours, and 1.5 mL of the pre-cultured medium was inoculated in the 50 mL modified M9 medium of a 350 mL flask and cultured.

The composition of the modified M9 medium contained 10 g glucose, 5 g glutamic acid, 6.78 g $Na_2HPO_4$, 3.0 g $KH_2PO_4$, 0.5 g NaCl, 1.0 g $NH_4Cl$, 1 mM $MgSO_4$, 0.1 mM $CaCl_2$, 10 mg thiamine per 1 liter distilled water. In the above composition, the glutamic acid was supplied as a carbon source for providing GABA in the microorganism. The culture was carried out in a shaking incubator (jSR, Korea) operating at 37° C. and 200 rpm for 48 hours. After the culture was completed, the culture solution was centrifuged at 13,200 rpm for 10 minutes, and only the supernatant was collected and subjected to HPLC-MS analysis to confirm the production of 2-pyrrolidone.

Figure 9:
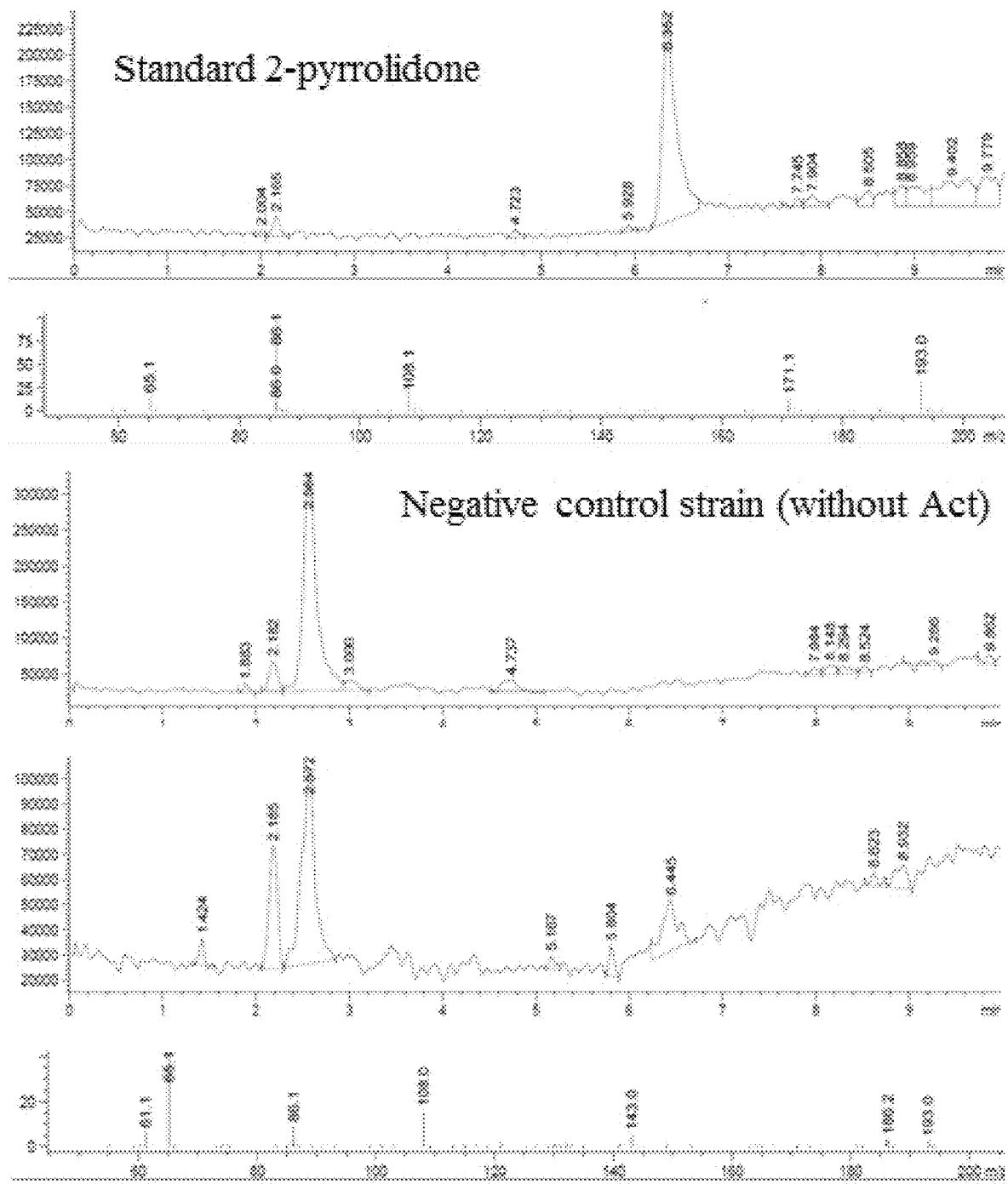
FIG. 9 shows the results of analysis of 2-pyrrolidone prepared by culturing the recombinant microorganism into which the vector is introduced.

As a result, as shown in FIG. 9, it was confirmed that the recombinant microorganism according to the present disclosure showed a peak at 6.445 minutes which is similar to that of 2-pyrrolidone standard substances, and an analysis of the peak showed that peaks were detected at m/z=86.0 and 108.0 which are the same as that of the standard 2-pyrrolidone, whereas the 2-pyrrolidone was not produced at all in the recombinant microorganism in which an empty vector was transformed.

From these results, it was confirmed that the recombinant microorganism according to the present disclosure successfully produced 2-pyrrolidone using glutamic acid as a carbon source.

4-2: Confirmation of Production of Valerolactam from Glucose Using Recombinant Microorganism The recombinant microorganism (XQ56/pKE112-davAB/pTac15k-act) prepared in Example 3-5 was inoculated into 10 mL of LB medium, pre-cultured at 37° C. for 8 hours, and 1.5 mL of the pre-cultured medium was inoculated in the 50 mL modified MR-3 medium of a 350 mL flask and cultured.

The composition of the modified MR-3 medium (pH 7.0) contained 10 g glucose, 9 g $(NH_4)_2SO_4$, 6.67 g $KH_2PO_4$, 4.0 g $(NH_4)_2HPO_4$, 0.8 g citric acid, 0.8 g $MgSO_4.7H_2O$, 0.01 g $CaCl_2.2H_2O$, 5 mL trace metal solution (10 g $FeSO_4.7H_2O$, 2.2 g $ZnSO_4.4H_2O$, 0.58 g $MnSO_4.4H_2O$, 1 g $CuSO_4.5H_2O$, 0.1 g $(NH_4)_6Mo_7O_{24}.4H_2O$, 0.02 g $Na_2B_4O_7.10H_2O$ per 1 liter distilled water) per 1 liter distilled water. The glucose was supplied as a carbon source in the above composition. The culture was carried out in a shaking incubator (jSR, Korea) operating at 37° C. and 200 rpm for 36 hours. After the culture was completed, the culture solution was centrifuged at 13,200 rpm for 10 minutes, and only the supernatant was collected and subjected to HPLC-MS analysis to confirm the production of valerolactam.

As a result, as shown in Table 3, it was confirmed that the recombinant microorganism according to the present disclosure produced 28.36 mg/L of valerolactam, whereas the valerolactam was not produced at all in the recombinant microorganism in which an empty vector was transformed.

From these results, it was confirmed that the recombinant microorganism according to the present disclosure successfully produced valerolactam using glucose as a carbon source.

TABLE 3

Production amount (mg/L) of valerolactam of recombinant microorganism

| Strain | Production amount of valerolactam (mg/L) |
|---|---|
| XQ56/pKE112-davAB/pTac15k | 0 |
| XQ56/pKE112-davAB/pTac15k-act | 28.36 |

4-3: Confirmation of Production of 2-Pyrrolidone from Glucose Using Recombinant Microorganism The recombinant microorganism (ATCC 13032/pEKEx1_act_gadB) prepared in Example 3-5 was inoculated in 5 mL of RG medium (40 g/L brain heart infusion, 10 g/L glucose, 10 g/L beef extract, 30 g/L sorbitol), pre-cultured at 30° C. for 12 hours, and 1.5 mL of the pre-cultured medium was inoculated in 50 mL GP1 medium of a 350 mL flask and cultured.

The composition of the GP1 medium (pH 7.0) contained 50 g glucose, 50 g $(NH_4)_2SO_4$, 1.0 g $K_2HPO_4$, 3.0 g urea, 0.4 g $MgSO_4.7H_2O$, 50 g peptone, 0.01 g $FeSO_4$, 0.01 g $MnSO_4.5H_2O$, 200 μg thiamine, 0.1 mM pyridoxal 5-phosphate hydrate, 50 μg biotin per 1 liter distilled water. The glucose was supplied as a carbon source in the above composition. The culture was carried out in a shaking incubator (jSR, Korea) operating at 30° C. and 200 rpm for 96 hours. After the culture was completed, the culture solution was centrifuged at 13,200 rpm for 10 minutes, and only the supernatant was collected and subjected to HPLC-MS analysis to confirm the production of valerolactam.

TABLE 4

Production amount (mg/L) of 2-pyrrolidone of recombinant microorganism

| Strain | Production amount of 2-pyrrolidone(mg/L) |
|---|---|
| ATCC 13032/pEKEx1_gadB | 0 |
| ATCC 13032/pEKEx1_act_gadB | 75.92 |

Although specific parts of the context of the present disclosure have been described in detail as above, those skilled in the art will appreciate that such specific descrip-tion is merely preferred exemplary embodiments and that the scope of the present disclosure is not limited thereto. Therefore, the actual scope of the present disclosure will be defined by the appended claims and their equivalents.

INDUSTRIAL APPLICABILITY

The recombinant microorganism of the present disclosure is capable of producing various lactam compounds such as propiolactam, 2-pyrrolidone, valerolactam, caprolactam, and heptanolactam from omega-amino acids, and thus is useful for industrial production of lactams.

What is claimed is:

1. A recombinant microorganism having an ability to produce lactam from an omega-amino acid, wherein a gene encoding a beta-alanine coenzyme A transferase having the amino acid sequence of SEQ ID NO: 2 is introduced into a microorganism which has an omega-amino acid biosynthetic metabolic pathway inherently or an omega-amino acid biosynthetic metabolic pathway is introduced.

2. The recombinant microorganism of claim 1, wherein the gene encoding the beta-alanine coenzyme A transferase is act obtained from *Clostridium propionicum*.

3. The recombinant microorganism of claim 1, wherein the lactam is selected from the group consisting of propiolactam, 2-pyrrolidone, valerolactam, caprolactam, heptanolactam, octanolactam, nonanolactam, decanolactam, undecanolactam, and dodecanolactam.

4. The recombinant microorganism of claim 1, wherein the omega-amino acid is selected form the group consisting of beta-alanine, gamma-aminobutyric acid (GABA), 5-aminovaleric acid (5AVA), 6-aminocaproic acid (6ACA), 7-aminoheptanoic acid (7AHA), 8-aminoooctanoic acid, 9-aminononanoic acid, 10-aminodecanoic acid, 11-aminoundecanoic acid, and 12-aminododecanoic acid.

5. The recombinant microorganism of claim 1, wherein the omega-amino acid biosynthesis metabolic pathway is gamma-aminobutyric acid (GABA) biosynthetic metabolic pathway.

6. The recombinant microorganism of claim 1, wherein the omega-amino acid biosynthesis metabolic pathway is 5-aminovaleric acid (5AVA) biosynthetic metabolic pathway.

7. The recombinant microorganism of claim 6, wherein the 5-aminovaleric acid (5AVA) biosynthetic metabolic pathway is introducing a gene encoding delta-aminovaleramidase and a gene encoding lysine 2-monooxygenase.

8. The recombinant microorganism of claim 7, wherein the gene encoding delta-aminovaleramidase is davA obtained from *Pseudomonas putida* and the gene encoding lysine 2-monooxygenase is davB obtained from *Pseudomonas putida*.

9. The recombinant microorganism of claim 1, wherein the omega-amino acid is biosynthesized from a carbon source selected from the group consisting of monosaccharides, disaccharides, and polysaccharides including glucose, sucrose, galactose, maltose, xylose, glycerol, fructose and sugar cane.

10. The recombinant microorganism of claim 1, wherein the recombinant microorganism is selected from the group consisting of bacteria, yeast, and fungi.

11. A method for preparing a lactam from an omega-amino acid comprising:
 (a) culturing the recombinant microorganism of claim 1 to produce a lactam; and
 (b) recovering the produced lactam.

12. A method for preparing a lactam from an omega-amino acid comprising:
 (a) mixing a beta-alanine coenzyme A transferase having the amino acid sequence of SEQ ID NO: 2 with a reaction solution containing the omega-amino acid and reacting to prepare an omega-amino acyl-CoA; and
 (b) preparing the lactam by forming a ring structure of the produced omega-amino acyl-CoA.

13. The method of claim 12, wherein a gene encoding the beta-alanine coenzyme A transferase is act obtained from *Clostridium propionicum*.

14. The method of claim 12, wherein the lactam is selected from the group consisting of propiolactam, 2-pyrrolidone, valerolactam, caprolactam, heptanolactam, octanolactam, nonanolactam, decanolactam, undecanolactam, and dodecanolactam.

15. The method of claim 12, wherein the omega-amino acid is selected form the group consisting of beta-alanine, gamma-aminobutyric acid (GABA), 5-aminovaleric acid (5AVA), 6-aminocaproic acid (6ACA), 7-aminoheptanoic acid (7AHA), 8-aminooctanoic acid, 9-aminononanoic acid, 10-aminodecanoic acid, 11-aminoundecanoic acid, and 12-aminododecanoic acid.

16. A method for preparing an omega-amino acyl-CoA from an omega-amino acid comprising:
 (a) culturing the recombinant microorganism of claim 1 to produce the omega-amino acyl-CoA; and
 (b) recovering the produced omega-amino acyl-CoA.

17. A method for preparing an omega-amino acyl-CoA from an omega-amino acid, comprising mixing a beta-alanine coenzyme A transferase having the amino acid sequence of SEQ ID NO: 2 in a reaction solution containing the omega-amino acid and then reacting to prepare the omega-amino acyl-CoA.

18. The method of claim 17, wherein a gene encoding the beta-alanine coenzyme A transferase is act obtained from *Clostridium propionicum*.

19. The method of claim 17, wherein the omega-amino acid is selected form the group consisting of beta-alanine, gamma-aminobutyric acid (GABA), 5-aminovaleric acid (5AVA), 6-aminocaproic acid (6ACA), 7-aminoheptanoic acid (7AHA), 8-aminooctanoic acid, 9-aminononanoic acid, 10-aminodecanoic acid, 11-aminoundecanoic acid, and 12-aminododecanoic acid.

* * * * *

SEQUENCE LISTING

<160> NUMBER OF SEQ ID NOS: 8

<210> SEQ ID NO 1
<211> LENGTH: 1194
<212> TYPE: DNA
<213> ORGANISM: Clostridium propionicum

<400> SEQUENCE: 1

```
atgaaaagac ccttggaagg tattcgtgta cttgatttaa cacaggctta cagtggcccc      60
ttttgtacaa tgaatcttgc tgatcatggt gctgaggtta ttaaaattga gcgccccggc     120
agtggagatc aaacaagagg ttgggggcct atggaaaatg actacagtgg ctactatgct     180
tacattaacc gtaataaaaa aggaatcacc ttaaatcttg cttccgaaga aggaaagaaa     240
gtttttgccg aattggttaa atctgccgat gtgatttgcg aaaactataa ggttggtgtt     300
ttagaaaaat taggcttttc ctatgaggtc ttaaaagaac tcaacccccg catcatttat     360
ggctccatca gcggttttgg attaacaggt gaattgtcct cccgcccctg ctatgatatc     420
gtcgctcaag caatgagcgg aatgatgagt gtaaccggct ttgcagacgg tcctccctgc     480
aaaatcggcc cttctgtagg agatagctat actggtgcat atttgtgcat gggtgttttg     540
atggcattat acgaaagaga aaaaacaggc gttggccgcc gtatcgatgt gggaatggta     600
gatacccctgt tctctacaat ggaaaacttt gttgttgaat acaccattgc tggtaagcat     660
ccccaccgtg caggcaatca agatccaagt attgcccctt ttgactcctt tagggcaaaa     720
gattcggatt ttgtaatggg gtgtggcaca aacaaaatgt ttgcaggact atgtaaagca     780
atgggcagag aggatttgat tgatgatcct cgtttcaata caaacctgaa tcgttgtgat     840
aactatttaa atgacttaaa gccaatcatc gaagaatgga cccaaacaaa gaccgttgca     900
gagttagagg aaatcatctg cggactttcc attcccttcg gcccaatcct cacgattccc     960
gagatttctg agcattcctt aacaaagaa agaaatatgc tttgggaagt ttatcagcct    1020
ggcatggata gaacaattcg cattcccggc tcccctatta aaatccacgg tgaagaagat    1080
aaggctcaga aaggtgcccc tattctggga gaagacaatt tgctgtcta cgcagaaatt    1140
ttaggtctct cagtagaaga aattaaatca ctggaagaga aaaatgtcat ctaa          1194
```

<210> SEQ ID NO 2
<211> LENGTH: 397
<212> TYPE: PRT
<213> ORGANISM: Clostridium propionicum

<400> SEQUENCE: 2

Met Lys Arg Pro Leu Glu Gly Ile Arg Val Leu Asp Leu Thr Gln Ala
1               5                   10                  15

Tyr Ser Gly Pro Phe Cys Thr Met Asn Leu Ala Asp His Gly Ala Glu

```
            20                  25                  30
Val Ile Lys Ile Glu Arg Pro Gly Ser Gly Asp Gln Thr Arg Gly Trp
            35                  40                  45
Gly Pro Met Glu Asn Asp Tyr Ser Gly Tyr Tyr Ala Tyr Ile Asn Arg
        50                  55                  60
Asn Lys Lys Gly Ile Thr Leu Asn Leu Ala Ser Glu Glu Gly Lys Lys
65                  70                  75                  80
Val Phe Ala Glu Leu Val Lys Ser Ala Asp Val Ile Cys Glu Asn Tyr
                85                  90                  95
Lys Val Gly Val Leu Glu Lys Leu Gly Phe Ser Tyr Glu Val Leu Lys
                100                 105                 110
Glu Leu Asn Pro Arg Ile Ile Tyr Gly Ser Ile Ser Gly Phe Gly Leu
                115                 120                 125
Thr Gly Glu Leu Ser Ser Arg Pro Cys Tyr Asp Ile Val Ala Gln Ala
            130                 135                 140
Met Ser Gly Met Met Ser Val Thr Gly Phe Ala Asp Gly Pro Pro Cys
145                 150                 155                 160
Lys Ile Gly Pro Ser Val Gly Asp Ser Tyr Thr Gly Ala Tyr Leu Cys
                165                 170                 175
Met Gly Val Leu Met Ala Leu Tyr Glu Arg Glu Lys Thr Gly Val Gly
                180                 185                 190
Arg Arg Ile Asp Val Gly Met Val Asp Thr Leu Phe Ser Thr Met Glu
            195                 200                 205
Asn Phe Val Val Glu Tyr Thr Ile Ala Gly Lys His Pro His Arg Ala
            210                 215                 220
Gly Asn Gln Asp Pro Ser Ile Ala Pro Phe Asp Ser Phe Arg Ala Lys
225                 230                 235                 240
Asp Ser Asp Phe Val Met Gly Cys Gly Thr Asn Lys Met Phe Ala Gly
                245                 250                 255
Leu Cys Lys Ala Met Gly Arg Glu Asp Leu Ile Asp Asp Pro Arg Phe
            260                 265                 270
Asn Thr Asn Leu Asn Arg Cys Asp Asn Tyr Leu Asn Asp Leu Lys Pro
            275                 280                 285
Ile Ile Glu Glu Trp Thr Gln Thr Lys Thr Val Ala Glu Leu Glu Glu
            290                 295                 300
Ile Ile Cys Gly Leu Ser Ile Pro Phe Gly Pro Ile Leu Thr Ile Pro
305                 310                 315                 320
Glu Ile Ser Glu His Ser Leu Thr Lys Glu Arg Asn Met Leu Trp Glu
                325                 330                 335
Val Tyr Gln Pro Gly Met Asp Arg Thr Ile Arg Ile Pro Gly Ser Pro
            340                 345                 350
Ile Lys Ile His Gly Glu Glu Asp Lys Ala Gln Lys Gly Ala Pro Ile
            355                 360                 365
Leu Gly Glu Asp Asn Phe Ala Val Tyr Ala Glu Ile Leu Gly Leu Ser
        370                 375                 380
Val Glu Glu Ile Lys Ser Leu Glu Glu Lys Asn Val Ile
385                 390                 395

<210> SEQ ID NO 3
<211> LENGTH: 53
<212> TYPE: DNA
<213> ORGANISM: Artificial Sequence
<220> FEATURE:
<223> OTHER INFORMATION: synthesized primer ckphisact (NdeI, F)
```

```
<400> SEQUENCE: 3
agacagcata tgcaccatca tcatcatcat aaaagaccct tggaaggtat tcg        53

<210> SEQ ID NO 4
<211> LENGTH: 39
<212> TYPE: DNA
<213> ORGANISM: Artificial Sequence
<220> FEATURE:
<223> OTHER INFORMATION: synthesized primer ckpact (SalI, R)

<400> SEQUENCE: 4
agacaggtcg acttagatga catttttctc ttccagtga                        39

<210> SEQ ID NO 5
<211> LENGTH: 36
<212> TYPE: DNA
<213> ORGANISM: Artificial Sequence
<220> FEATURE:
<223> OTHER INFORMATION: synthesized primer ckpact (EcoRI, F)

<400> SEQUENCE: 5
agacaggaat tcatgaaaag acccttggaa ggtatt                           36

<210> SEQ ID NO 6
<211> LENGTH: 38
<212> TYPE: DNA
<213> ORGANISM: Artificial Sequence
<220> FEATURE:
<223> OTHER INFORMATION: synthesized primer ckpact (SacI, R)

<400> SEQUENCE: 6
agacaggtcg acttagatga catttttctc ttccagtg                         38

<210> SEQ ID NO 7
<211> LENGTH: 53
<212> TYPE: DNA
<213> ORGANISM: Artificial Sequence
<220> FEATURE:
<223> OTHER INFORMATION: synthesized primer ecjgadB (BamHI, RBS, F)

<400> SEQUENCE: 7
agacagggat cctttcacac aggaaacaat ggataagaag caagtaacgg att        53

<210> SEQ ID NO 8
<211> LENGTH: 38
<212> TYPE: DNA
<213> ORGANISM: Artificial Sequence
<220> FEATURE:
<223> OTHER INFORMATION: synthesized primer ecjgadB (SalI, R)

<400> SEQUENCE: 8
agacaggtcg actcaggtat gtttaaagct gttctgtt                         38
```